US010849906B2

(12) United States Patent
Xie et al.

(10) Patent No.: US 10,849,906 B2
(45) Date of Patent: Dec. 1, 2020

(54) USE OF AKT2 IN DIAGNOSIS AND TREATMENT OF TUMOR

(71) Applicant: Yanhui Xie, Shanghai (CN)

(72) Inventors: Yanhui Xie, Shanghai (CN); Mixue Xie, Hangzhou (CN)

(73) Assignee: Yanhui Xie, Shanghai (CN)

( * ) Notice: Subject to any disclaimer, the term of this patent is extended or adjusted under 35 U.S.C. 154(b) by 103 days.

(21) Appl. No.: 15/778,479

(22) PCT Filed: Nov. 30, 2015

(86) PCT No.: PCT/CN2015/096011
§ 371 (c)(1),
(2) Date: May 23, 2018

(87) PCT Pub. No.: WO2017/091952
PCT Pub. Date: Jun. 8, 2017

(65) Prior Publication Data
US 2020/0000809 A1    Jan. 2, 2020

(51) Int. Cl.
| | |
|---|---|
| *A61K 31/52* | (2006.01) |
| *A61P 35/02* | (2006.01) |
| *A61K 31/7088* | (2006.01) |
| *C07K 16/22* | (2006.01) |
| *A61K 45/06* | (2006.01) |
| *A61K 49/00* | (2006.01) |

(52) U.S. Cl.
CPC .......... *A61K 31/52* (2013.01); *A61K 31/7088* (2013.01); *A61P 35/02* (2018.01); *C07K 16/22* (2013.01); *A61K 45/06* (2013.01); *A61K 49/00* (2013.01)

(58) Field of Classification Search
CPC ........ A61K 31/106; A61K 45/00; A61P 35/02
USPC ..... 435/6.1, 91.1, 91.31, 455, 458; 514/1, 2, 514/44 A; 536/23.1, 24.5
See application file for complete search history.

(56) References Cited

U.S. PATENT DOCUMENTS

2004/0043023 A1    3/2004   Vedeckis et al.

OTHER PUBLICATIONS

Ester Borroni, in her Doctoral Thesis, Università degli Studi del Piemonte Orientale Amedeo Avogadro, Dipartimento di Scienze del Farmaco, Dottorato di Ricerca in Biotecnologie Farmaceutiche ed Alimentari XXVI ciclo A. A. 2010-2013 (Year: 2013).*
Sabbineni, et al; Genetic deletion and pharmacological inhibition of Akt1 isoform attenuates bladder cancer cell proliferation, motility and invasion; Eur J Pharmacol; Oct. 5, 2015; 764:208-214.
Wang, et al; CCT128930 induces cell cycle arrest, DNA damage, and autophagy independent of Akt inhibition; Biochimie; 2014; 1-8.
Yap, et al; Preclinical Pharmacology, Antitumor Activity, and Development of Pharmacodynamic Markers for the Novel, Potent AKT Inhibitor CCT128930; Mol Cancer Ther; 10(2); Feb. 2011; 360-371.
State Intellectual Property Office of the P.R. China; International Search Report for PCT/CN2015/096011; dated Aug. 10, 2016.
Meinig, et al.; Anticancer/Antiviral Agent Akt Inhibitor-IV Massively Accumulates in Mitochondria and Potently Disrupts Cellular Bioenergetics; ACS Chemical Biology; Nov. 21, 2014; vol. 10; 570-576.
Fillmore, et al.; Expression of Akt (protein kinase B) and its isoforms in malignant lymphomas; Leukemia and Lymphoma; Dec. 2005; vol. 46; 1765-1773.
Hulleman, et al; Inhibition of glycolysis modulates prednisolone resistance in acute lymphoblastic leukemia cells; Blood; Feb. 2009; vol. 113; 2014-2021.
Rimi, et al; Glucocorticoid receptor heterozygosity combined with lack of receptor auto-induction causes glucocorticoid resistance in Jurkat acute lymphoblastic leukemia cells; Cell Death and Differentiation; 2004; vol. 11; S65-S72.
Piovan, et al; Direct Reversal of Glucocorticoid Resistance by AKT Inhibition in Acute Lymphoblastic Leukemia; Cancer Cell; 2013; vol. 24, 766-776.
Blackburn, et al; Clonal Evolution Enhances Leukemia-Propagating Cell Frequency in T Cell Acute Lymphoblastic Leukemia through Akt/mTORC1 Pathway Activation; Cancer Cell; 2014; vol. 25; 366-378.
Hirai, et al; MK-2206, an Allosteric Akt Inhibitor, Enhances Antitumor Efficacy by Standard Chemotherapeutic Agents or Molecular Targeted Drugs in vitro and in vivo; Mol. Cancer Therapeutics; Jun. 2010; vol. 9; 1956-1967.
Cani, et al; Triple Akt inhibition as a new therapeutic strategy in T-cell acute lymphoblastic leukemia; Mar. 2015; vol. 6, No. 6; 6597-6610.
Japanese Patent Office; Office Action dated Aug. 2, 2019; Japanese Patent Appl. No. 2018-546727.
Sibylle Gundisch:"Glucocorticoids Augment Survival and Proliferation of Tumor Cells", Anticancer Research, Aug. 7, 2012 (Aug. 7, 2012), pp. 4251-4261, XP055588941, Retrieved from the Internet: URL:http://ar.iiarjournals.org/content/32/10/4251.full .pdf [retrieved on May 15, 2019].
C. P. Hall et al: "Modulation of Glucocorticoid Resistance in Pediatric T-cell Acute Lymphoblastic Leukemia by Increasing BIM Expression with the PI3K/mTOR Inhibitor BEZ235", Clinical Cancer Research, vol. 22, No. 3, Jun. 16, 2015 (Jun. 16, 2015), pp. 621-632, XP055588957, & Meeting of the American-Association-for-Cancer-Research (AACR) Precision Medicine Series—Integrati; Salt Lake, UT, USA; Jun. 13-16, 2015 ISSN: 1078-0432, DOI:10 .1158/1078-0432. CCR-15-0114.

(Continued)

*Primary Examiner* — Jane J Zara
(74) *Attorney, Agent, or Firm* — Kilpatrick Townsend & Stockton LLP

(57) ABSTRACT

Provided is use of a pharmaceutical composition in treating a glucocorticoid-resistant tumor characterized by an increased level of Akt2 expression. The pharmaceutical composition comprises an Akt2 inhibitor, a glucocorticoid, and optionally a pharmaceutically acceptable carrier, excipient and/or diluent. Also provided are use of an Akt2 detecting agent in detecting a glucocorticoid-resistant tumor, and use of an Akt2 inhibitor in the preparation of a pharmaceutical composition for treating a tumor.

20 Claims, 18 Drawing Sheets
Specification includes a Sequence Listing.

(56) References Cited

OTHER PUBLICATIONS

Erich Piovan et al:"Direct Reversal of Glucocorticoid Resistance by AKT Inhibition in Acute Lymphoblastic Leukemia", Cancer Cell, vol. 24, No. 6, Dec. 1, 2013 (Dec. 1, 2013), 766-776, XP055589297, US ISSN: 1535-6108, DOI: 10 .1016/ j. ccr. 2013 .10. 022.

Blackburn Jessica S et al: "Clonal Evolution Enhances Leukemia-Propagating Cell Frequency in T Cell Acute Lymphoblastic Leukemia Through Akt/mTORC1 Pathway Activation", Cancer Cell, Cell Press, US, vol. 25, No. 3, Mar. 6, 2014 (Mar. 6, 2014), pp. 366-378, XP028633342, ISSN: 1535-6108, DOI:10.1016/J.CCR. 2014.01.032 * abstract *.

H. Hirai et al: "MK-2206, an Allosteric Akt Inhibitor, Enhances Antitumor Efficacy by Standard Chemotherapeutic Agents or Molecular Targeted Drugs In vitro and In vivo", Molecular Cancer Therapeutics, vol. 9, No. 7, Jul. 1, 2010 (Jul. 1, 2010), pp. 1956-1967, XP055074270, ISSN: 1535-7163, DOI:10.1158/1535-7163.MCT-09-1012.

T. A. Yap et al: "Preclinical Pharmacology, Antitumor Activity, and Development of Pharmacodynamic Markers the Novel, Potent AKT Inhibitor CCT128930", Molecular Cancer Therapeutics, vol. 10, No. 2, Feb. 1, 2011 (Feb. 1, 2011), 360-371, XP055589234, US ISSN: 1535-7163, DOI:10.1158/1535-7163.MCT-10-0760.

Mixue Xie et al:"Akt2 mediates glucocorticoid resistance in lymphoid malignancies through Fox03a/Bim axis and serves as a direct target for resistance reversal", Cell Death & Disease, vol. 9, No. 10, Oct. 1, 2018 (Oct. 1, 2018), XP055587571, DOI: 10.1038/s41419-018-1043-6

European Patent Office: Extended European Search Report for EP 15909467.7; National phase entry for PCT/CN2015/096011; dated Jul. 8, 2019.

Japan Patent Office; Notification of Reason for Rejection; Japanese Patent Application No. 2018-546727; dated Jun. 16, 2020.

* cited by examiner

SGK inhibitor in T and B Lymphocytes

SEQUENCE LISTING

```
<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gctggacgat agcttgga                                                    18

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
gatgacagat agctggtg                                                    18

<210> SEQ ID NO 3
<211> LENGTH: 19
<212> TYPE: DNA
<213> ORGANISM: Artificial Sequence
<220> FEATURE:
```

```
<223> OTHER INFORMATION: primer

<400> SEQUENCE: 3
ggcccctgat cagactcta                                                19

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
tcctcagtcg tggaggagt                                                19

<210> SEQ ID NO 5
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (20)..(21)
<223> OTHER INFORMATION: n is t

<400> SEQUENCE: 5
ggcccaacac cuucaucaun n                                             21

<210> SEQ ID NO 6
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (20)..(21)
<223> OTHER INFORMATION: n is t

<400> SEQUENCE: 6
augaugaagg uguugggccn n                                             21

<210> SEQ ID NO 7
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (20)..(21)
<223> OTHER INFORMATION: n is t

<400> SEQUENCE: 7
gguucuuccu cagcaucaan n                                             21

<210> SEQ ID NO 8
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (20)..(21)
<223> OTHER INFORMATION: n is t
```

```
<400> SEQUENCE: 8
uugaugcuga ggaagaaccn n                                             21
```

USE OF AKT2 IN DIAGNOSIS AND TREATMENT OF TUMOR

CROSS-REFERENCE TO RELATED APPLICATIONS

This application is a National Phase Entry of PCT/CN2015/096011, filed Nov. 30, 2015, the teachings of which are hereby incorporated by reference in their entireties for all purposes.

REFERENCE TO A "SEQUENCE LISTING" SUBMITTED AS ASCII TEXT FILES VIA EFS-WEB

The Sequence Listing written in file 103792-000300US-1088618_SubstituteSequenceListing.txt created on Jan. 7, 2019, 1,974 bytes, machine format IBM-PC, MS-Windows operating system, in accordance with 37 C.F.R. §§ 1.821- to 1.825, is hereby incorporated by reference in its entirety for all purposes.

TECHNICAL FIELD

The present invention belongs to the field of biology and medicine, relating to tumor diagnosis and treatment, in particular to a detecting agent for Akt kinase subtype, Akt2, for diagnosing a glucocorticoid resistant tumor and a combination of an Akt2 inhibitor and a glucocorticoid for treating a tumor, particularly lymphocytic leukemia, myeloma and lymphoma.

BACKGROUND ART

The PI3K/Akt pathway, widely existed in cells, is a signaling pathway participated in regulating the growth, proliferation and differentiation of cells, and closely related to the incidence and development of various tumors in human beings. Akt1 and Akt2, as Akt subtypes, both play a role in regulating cell growth and proliferation and regulating blood glucose level. Studies have shown that Akt1 is an important target responsible for glucocorticoid resistance in cells. However, there is no report on the correlation of Akt2 to the occurrence/development, drug resistance and prognosis of lymphocyte-derived tumors.

Glucocorticoid (GC) is one of the clinically effective drugs that can induce apoptosis of lymphocytes and used as first-line chemotherapy of various hemolymphatic tumors. Glucocorticoid resistance is a common problem in the clinical treatment of lymphatic tumors and is an important cause of treatment failure. At present, although there has been some progress in the study about glucocorticoid resistance, the particular molecular mechanism of resistance is still unclear. Recent studies have found that glucocorticoid resistance is not related to the increased number of glucocorticoid receptor (GR), structural function of GR, expression of molecular chaperones and gene mutation, and GR mutation is extremely rare; Prednisone resistance is not related to multidrug resistance genes (such as ABCB1, ABCB4, ABCC1, ABCG2 and MVP); Other studies have found that many target genes may lead to glucocorticoid resistance, and it is preliminarily believed that glucocorticoid sensitivity and resistance are mediated by different cell signaling pathways. Accordingly, we need a new method for treating glucocorticoid resistant tumors.

SUMMARY OF THE INVENTION

In an aspect, the present invention provides a method for diagnosing a glucocorticoid resistant tumor, comprising measuring the expression of Akt2 in tumor cells, wherein the elevated expression of Akt2 in the measured tumor cells relative to glucocorticoid sensitive tumor cells indicates that the tumor is glucocorticoid resistant.

In another aspect, the present invention provides use of a detecting agent for the detection of Akt2, such as an antibody to Akt2 protein, or a probe or primer for the detection of Akt2 mRNA, in the preparation of a composition or kit for diagnosing a glucocorticoid resistant tumor.

In another aspect, the present invention provides a detecting agent for the detection of Akt2, such as an antibody to Akt2 protein, or a probe or primer for the detection of Akt2 mRNA, for use in diagnosing a glucocorticoid resistant tumor.

In another aspect, the present invention provides a method for treating a tumor, for example, for improving the sensitivity of a tumor to glucocorticoid therapy or treating a glucocorticoid resistant tumor, comprising administering to a patient with the tumor a therapeutically effective amount of an Akt2 inhibitor and a glucocorticoid.

In another aspect, the present invention provides a pharmaceutical composition for treating a tumor, for example, improving or increasing the sensitivity of a tumor to glucocorticoid therapy or treating a glucocorticoid resistant tumor, comprising an Akt2 inhibitor and a glucocorticoid and optionally a pharmaceutically acceptable carrier, excipient and/or diluent.

In another aspect, the present invention provides use of an Akt2 inhibitor in the preparation of a pharmaceutical composition for treating a tumor, for example, for improving the sensitivity of a tumor to glucocorticoid therapy or for treating a glucocorticoid resistant tumor. In an embodiment, the pharmaceutical composition comprises a glucocorticoid and optionally a pharmaceutically acceptable carrier, excipient and/or diluent.

In another aspect, the present invention provides an Akt2 inhibitor for use in treating a tumor, for example, for improving the sensitivity of a tumor to glucocorticoid therapy or for treating a glucocorticoid resistant tumor.

In an embodiment of the present invention, the tumor is a lymphocyte-derived tumor, such as lymphocytic leukemia, lymphoma such as B-cell lymphoma or T-cell lymphoma or myeloma. In an embodiment of the present invention, the tumor is a T cell-derived tumor, such as T-lymphocytic leukemia, T-cell lymphoma and myeloma. In an embodiment of the present invention, the lymphocytic leukemia is selected from the group consisting of acute lymphocytic leukemia and chronic lymphocytic leukemia. In an embodiment, the tumor is acute T-lymphocytic leukemia.

In an embodiment of the present invention, the glucocorticoid is selected from the group consisting of dexamethasone, betamethasone, triamcinolone, triamcinolone acetonide, beclomethasone, prednisolone, prednisone, methylprednisolone, hydrocortisone, cortisone acetate, budesonide, beclomethasone dipropionate, ciclesonide, cortisone, methylprednisolone, clobetasol butyrate, fluocinonide, beclomethasone dipropionate, mometasone furoate, halcinonide, clobetasol propionate, halcinonide, halometasone, diflorasone diacetate and derivatives thereof.

BRIEF DESCRIPTION OF THE DRAWINGS

FIG. 1A: CCRF-CEM flow cytometry: the apoptosis of CCRF-CEM cells induced by different concentrations of dexamethasone. FIG. 1B: Western blot of protein expression in Akt/FoxO3a/Bim signaling pathway in CCRF-CEM cells after treated with dexamethasone. p-Akt: phosphorylated Akt, p-FoxO3a: phosphorylated FoxO3a. FIG. 1C: the apoptosis of CEM-DR cells induced by different concentrations of dexamethasone. FIG. 1D: the protein expression of Akt/FoxO3a/Bim signaling pathway in CCRF-CEM and CEM-DR cells.

FIG. 2A: the apoptosis of CCRF-CEM cells in each group treated with an Akt inhibitor and a PI3K inhibitor LY294002. FIG. 2B: western blot of protein expression of Akt/FoxO3a/Bim signaling pathway in CCRF-CEM cells in each group treated with an Akt inhibitor and a PI3K inhibitor LY294002. FIG. 2C: the apoptosis of CCRF-CEM cells treated with different concentrations of an Akt inhibitor in combination with dexamethasone. FIG. 2D: the apoptosis of CCRF-CEM cells treated with an Akt inhibitor. FIG. 2E: the apoptosis of Molt-4 cells in each group treated with an Akt inhibitor and a PI3K inhibitor LY294002. FIG. 2F: the apoptosis of Jurkat cells in each group treated with an Akt inhibitor and a PI3K inhibitor LY294002. FIG. 2G: the apoptosis of CCRF-CEM cells in each group treated with 2-DG. FIG. 2H: the protein expression of Akt/FoxO3a/Bim signaling pathway in CCRF-CEM cells of each group treated with 2-DG. FIG. 2I: western blot of FoxO3a protein expression in CCRF-CEM cells of each group treated with a Notch1 pathway inhibitor dapt. FIG. 2J: the apoptosis of CCRF-CEM cells in each group treated with a Notch1 pathway inhibitor dapt. FIG. 2K: the apoptosis of tumor lymphocytes treated with a SGK inhibitor GSK. FIG. 2L: the apoptosis of CCRF-CEM cells treated with an Akt inhibitor as compared to other cell proliferation pathway inhibitors. FIG. 2M: the apoptosis of SP2/0 cells treated with an Akt inhibitor. FIG. 2N: the apoptosis of Raji cells treated with an Akt inhibitor.

FIG. 3A: the tumor formation of CCRF-CEM tumor-bearing mice in each group. FIG. 3B: the subcutaneous tumor size of CCRF-CEM tumor-bearing mice in each group. FIG. 3C: the tumor HE staining of CCRF-CEM tumor-bearing mice in each group. FIG. 3D: the comparison of overall survival of tumor-bearing mice in each group. FIG. 3E: the apoptosis of spleen cells in tumor-bearing mice in each group. FIG. 3F: the levels of liver transaminases ALT and AST of tumor-bearing mice in each group after drug administration.

FIG. 4A: the apoptosis of CCRF-CEM cells induced by 0.1 μM dexamethasone in combination with different concentrations of Akt1, Akt2 or Akt1/2 inhibitors. FIG. 4B: the viability of CCRF-CEM cells treated with different concentrations of dexamethasone in combination with an Akt subtype inhibitor. FIG. 4C: the apoptosis of CCRF-CEM cells in each group treated with an Akt subtype inhibitor. FIG. 4D: the apoptosis of CCRF-CEM cells in each group treated with an Akt subtype inhibitor. FIG. 4E: the viability of CCRF-CEM cells in each group treated with an Akt subtype inhibitor in combination with dexamethasone at fixed concentration ratio. FIG. 4F: the dexamethasone IC50 values of CCRF-CEM cells in each group treated with an Akt subtype inhibitor. FIG. 4G: the viability of CEM-DR cells treated with different concentrations of dexamethasone in combination with an Akt subtype inhibitor. FIG. 4H: the apoptosis of CEM-DR cells in each group treated with an Akt subtype inhibitor. FIG. 4I: the viability of CEM-DR cells in each group treated with an Akt subtype inhibitor in combination with dexamethasone at fixed concentration ratio. FIG. 4J: the apoptosis of Jurkat cells in each group treated with an Akt subtype inhibitor. FIG. 4K: the viability of Jurkat cells in each group treated with an Akt subtype inhibitor in combination with dexamethasone at fixed concentration ratio. FIG. 4L: the apoptosis of Daudi cells in each group treated with an Akt subtype inhibitor. FIG. 4M: the apoptosis of Daudi cells in each group treated with an Akt subtype inhibitor in combination with dexamethasone at fixed concentration ratio. FIG. 4N: the dexamethasone IC50 values of CEM-DR, Jurkat, Daudi cells treated with an Akt subtype inhibitor.

FIG. 5A: the expression of total and phosphorylated Akt1 and Akt2 proteins in CCRF-CEM cells in each group. FIG. 5B: the expression of total FoxO3a protein in CCRF-CEM cells in each group. FIG. 5C: the expression of phosphorylated FoxO3a protein in CCRF-CEM cells in each group. FIG. 5D: the expression of Bim protein in CCRF-CEM cells in each group. FIG. 5E: the expression levels of Akt1 and Akt2 in a variety of lymphoma cells and liver cells. FIG. 5F: a fluorescence diagram of siRNA-transfected Jurkat cells. FIG. 5G: the expression of Akt1 and Akt2 proteins in siRNA-transfected Jurkat cells in each group. FIG. 5H: the apoptosis of siRNA-transfected Jurkat cells in each group. FIG. 5I: the expression levels of Akt1 mRNA and Akt2 mRNA in lymphocytes of patients with initially treated or refractory relapsed acute lymphocytic leukemia. FIG. 5J: ROC analysis of Akt2 mRNA in lymphocytes of patients with initially treated or refractory acute lymphocytic leukemia.

FIG. 6A: the inhibition of Akt1 and Akt2 inhibitors in combination with dexamethasone on cell viability of healthy liver cells L-02. FIG. 6B: the expression of total and phosphorylated Akt subtype proteins in L-02 cells treated with Akt1 and Akt2 inhibitors. FIG. 6C: the expression of total FoxO3a protein in L-02 cells after 24-hour treated with an Akt subtype inhibitor. FIG. 6D: the expression of phosphorylated FoxO3a protein in L-02 cells after 24-hour treated with an Akt subtype inhibitor. FIG. 6E: the expression of Bim protein in L-02 cells after 24-hour treated with an Akt subtype inhibitor. FIG. 6F: the comparison of viability of liver cells L-02 after 24-hour treated with an Akt subtype inhibitor. FIG. 6G: the level of peripheral blood alanine aminotransferase (ALT) of nude mice in each group. FIG. 6H: the level of peripheral blood aspartate aminotransferase (AST) of nude mice in each group. FIG. 6I: the level of peripheral blood total bilirubin (TBIL) of nude mice in each group. FIG. 6J: the counting of peripheral blood leukocytes of nude mice in each group. FIG. 6K: the counting of peripheral blood erythrocytes of nude mice in each group. FIG. 6L: the level of peripheral blood hemoglobin of nude mice in each group. FIG. 6M: the counting of peripheral blood platelets of nude mice in each group. FIG. 6N: the level of blood glucose of nude mice in each group. FIG. 6O: the level of peripheral blood creatinine of nude mice in each group.

FIG. 7A: the subcutaneous tumor size of CCRF-CEM tumor-bearing mice in each group after drug administration. FIG. 7B: the subcutaneous tumor size of CCRF-CEM tumor-bearing mice in each group after drug administration. FIG. 7C: the spleen size of CCRF-CEM tumor-bearing mice in each group after drug administration. FIG. 7D: the overall survival of CCRF-CEM tumor-bearing mice in each group after drug administration.

FIG. 7E: the tumor HE staining of nude mice in each group: arrows pointing to the necrotic areas within tumor. FIG. 7F: the tumor Ki-67 staining of nude mice in each group. FIG. 7G: the spleen HE staining of nude mice in each group. FIG. 7H: the spleen CD3 staining of nude mice in each group. FIG. 7I: the spleen TDT staining of nude mice in each group.

FIG. 8A: the pathological sections of the liver of nude mice in each group (HE: 10*20). FIG. 8B: the pathological sections of the liver of nude mice in each group (HE: 10*40). FIG. 8C: the pathological sections of the heart of nude mice in each group (HE: 10*20). FIG. 8D: the pathological sections of the lung of nude mice in each group (HE: 10*20). FIG. 8E: the pathological sections of the kidney of nude mice in each group (HE: 10*20).

DETAILED DESCRIPTION OF THE INVENTION

Figure 1:
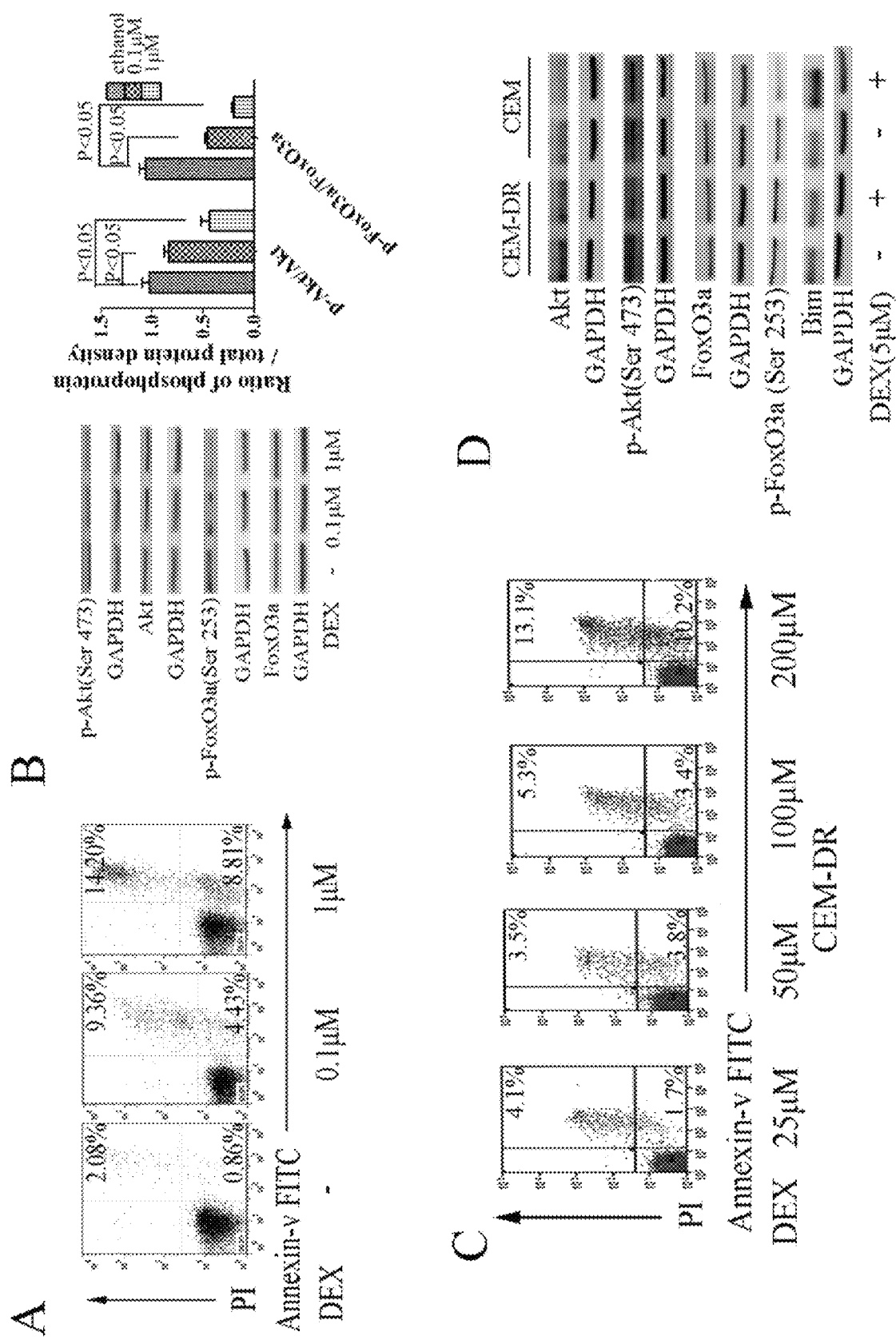
FIG. 1: the correlation of dexamethasone and the protein expression in Akt/FoxO3a pathway.

Unless otherwise indicated, all technical and scientific terms have the meaning commonly used by those skilled in the art. Unless otherwise indicated, all patents, patent applications, publications, GenBank sequences, websites, and other published materials are hereby incorporated by reference. In case there are several definitions to a term used herein, the definition in this section prevails. When describing a URL or another identifier or address, it should be understood that it may be changed and updated according to the information on the Internet at any time, and that related information may be found by searching the Internet. The disclosure may be used as a basis for the public availability.

The inventor has found that the expression of Akt2 in glucocorticoid resistant tumor cells is increased as compared to glucocorticoid sensitive cells. By using an Akt2 inhibitor to inhibit Akt2 protein, the sensitivity of glucocorticoid-resistant tumor cells to glucocorticoids is increased. In T-lymphoid tumor cells, an Akt2 subtype inhibitor significantly increases the sensitivity of glucocorticoid-induced lymphocyte apoptosis. In drug-resistant cell lines, the combination of an Akt2 subtype inhibitor and a glucocorticoid exhibits a good synergistic effect and are capable of reversing glucocorticoid resistance. An Akt2 subtype inhibitor can significantly down-regulate the intracellular p-FoxO3a/total FoxO3a ratio, up-regulate the expression of pro-apoptosis protein Bim, and improve glucocorticoid-induced lymphocyte apoptosis by enhancing the intracellular FoxO3a/Bim signaling pathway, thereby increasing the sensitivity of lymphocytes to a glucocorticoid.

Without being limited by any theory, the inventor believes that the expression of Akt2 protein is related to the sensitivity of cells to glucocorticoid, and the overexpression of Akt2 protein in cells may be an important mechanism responsible for glucocorticoid resistance in lymphocytes. Akt2 may be used as a more accurate therapy target for reversing glucocorticoid resistance of lymphoid tumors, also as a target for enhancing the sensitivity of lymphoid tumors to glucocorticoid treatment, and also as an indicative for predicting whether lymphocytes are glucocorticoid resistant or not.

In vivo and in vitro tests have confirmed that an Akt2 subtype inhibitor has the minimum toxicity, and has no effect on the blood system, liver functions, renal functions and blood glucose level in mice. An Akt2 subtype inhibitor can synergize with a glucocorticoid (such as dexamethasone) to effectively reduce the tumor size and spleen size in tumor-bearing mice, cause liquefaction and necrosis of a tumor, and increase the overall survival time; and an Akt2 subtype inhibitor is a medicament that has the best glucocorticoid sensitization effect and the minimum toxic side effects.

Accordingly, in one aspect, the present invention provides a method for diagnosing a glucocorticoid resistant tumor, comprising measuring the level of Akt2 in tumor cells, wherein the elevated level of Akt2 in the measured tumor cells relative to the glucocorticoid sensitive tumor cells indicates that the tumor is glucocorticoid resistant.

In the present invention, an increase in Akt2 level refers to elevated expression of Akt2 protein and/or increased activity of Akt2 protein. The measurement of Akt2 expression level can be performed by various methods of measuring expression known in the art, for example, measuring the level of mRNA at nucleic acid level or measuring the level of proteins at protein level. The measurement of activity of Akt2 protein can also be performed by various methods known in the art for measuring Akt2 activity, such as phosphorylation activity.

In the present invention, a glucocorticoid sensitive tumor refers to a tumor that exhibits a value of half maximal inhibitory concentration (IC50) for tumor cells of less than 10 μM (<10 μM) and can be effectively alleviated by clinically applying a regimen involving glucocorticoid treatment. For example, if the value of half maximal inhibitory concentration (IC50) for tumor cells is less than 10 μM (<10 μM), the tumor is a dexamethasone sensitive tumor.

In the present invention, a glucocorticoid resistant tumor refers to a tumor that exhibit a value of half maximal inhibitory concentration (IC50) for tumor cells of greater than or equal to 10 μM (≥10 μM), which exhibits tolerance to a glucocorticoid, resulting in decreased therapeutic effect of a glucocorticoid. As compared to a glucocorticoid sensitive tumor, a glucocorticoid resistant tumor requires more glucocorticoids to achieve the same therapeutic effect or even cannot be effectively treated with a glucocorticoid. For example, if the value of half maximal inhibitory concentration (IC50) for tumor cells is greater than or equal to 10 μM (≥10 μM), the tumor is a dexamethasone resistant tumor.

In the present invention, the glucocorticoid is any glucocorticoid drug that can be used by those skilled in the art for tumor treatment. In an embodiment of the present invention, the glucocorticoid is selected from the group consisting of dexamethasone, betamethasone, triamcinolone, triamcinolone acetonide, beclomethasone, prednisolone, prednisone, methylprednisolone, hydrocortisone, cortisone acetate, budesonide, beclomethasone dipropionate, ciclesonide, cortisone, methylprednisolone, clobetasol butyrate, fluocinonide, beclomethasone dipropionate, mometasone furoate, halcinonide, clobetasol propionate, halcinonide, halometasone, diflorasone diacetate and derivatives thereof. In an embodiment of the present invention, the glucocorticoid is dexamethasone or a derivative thereof.

As used herein, the "elevated or increased level" can be determined as follows, for example, glucocorticoid sensitive tumor cells are used as control group, the range of Akt2 protein level in the cells of the control group is determined, and then if the corresponding level of Akt2 protein in tumor cells to be measured is higher than the range of Akt2 protein level in cells of the control group, the level of Akt2 protein in the tumor cells to be measured is considered as "elevated or increased".

As used herein, the "elevated or increased level" refers to that as compared to a reference value (e.g., the median or mean value observed in glucocorticoid sensitive tumor cells), the measured value is increased, for example, by at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% or more.

In the present invention, the Akt2 level can be measured by using an Akt2 detecting agent. The Akt2 detecting agent refers to a molecule or compound capable of detecting Akt2 at protein and/or nucleic acid level, particularly at mRNA level, which may be a polypeptide, a nucleic acid, a carbohydrate, a lipid, a small molecular weight compound, an oligonucleotide, an oligopeptide, an RNA interference (RNAi), an antisense RNA, a recombinant protein, an antibody, or a conjugate or fusion protein thereof. For RNAi, please see Milhavet O, Gary D S, Mattson M P. (Pharmacol Rev. 2003 December; 55(4):629-48. Review.), for antisense RNA, please see Opalinska J B, Gewirtz A M. (Sci STKE. 2003 Oct. 28; 2003(206):pe47). For example, in order to determine the level of Akt2 protein in a patient suspected of having a glucocorticoid resistant tumor, the method according to the present invention can use an Akt2 protein-binding ligand to determine the level (concentration or absolute amount) of Akt2 protein in a tumor sample from the patient, wherein an elevated level of Akt2 protein in the sample indicates the presence of glucocorticoid resistant tumor in the patient.

As used herein, the ligand can be a receptor targeting agent, a cytokine, a hormone, a growth factor, a receptor-specific antibody, and a pattern recognition receptor (PRR) ligand. In an embodiment, the ligand is an antibody (or antigen-binding fragment thereof). The Akt2 protein in a sample can be revealed or analyzed using any technique known to a person skilled in the art, particularly using, for example, a specific ligand, such as an antibody or a fragment or an antibody derivative. Preferably, the ligand is an Akt2 protein-specific antibody or a fragment thereof (such as Fab, Fab', CDR etc.) or a derivative thereof (such as a single chain antibody, ScFv). The presence or amount of a target protein in a sample can be detected by detecting a target-ligand complex, for example, using a labeled ligand, using a second labeled detection ligand, or the like. A well-known immunology technique can be used, including ELISA, RIA and the like.

As used herein, the term "antibody", "antigen binding fragment" or "immunogenic part" has the meaning commonly known to those skilled in the art. For example, an "antigen-binding fragment" of an antibody is produced by recombinant DNA technique or enzymatic digestion or chemical cleavage of an intact antibody, including Fab, Fab', F(ab')$_2$, Fv, and a single-chain antibody (svFc). The antibody may be a polyclonal antibody, a monoclonal antibody, a chimeric antibody, a humanized antibody, a human antibody, and an antibody that may be labeled, as well as a fragment, variant or derivative thereof. The antibody label may be a radioactive label, a fluorescent label, an enzyme label, a chemiluminescent label, or a biotin group label.

The preparation or use of an antibody or a fragment thereof is well known. An antibody specific for a target protein can be produced by conventional techniques, particularly by immunizing a non-human animal with an immunogen comprising the protein (or an immunogenic fragment thereof) and recovering an antibody (polyclonal) or producing cells (to produce a monoclonal antibody). The techniques for preparing a polyclonal or monoclonal antibody, a ScFv fragment and a human or humanized antibody are described, for example, in the following: Harlow et al., Antibodies: A Laboratory Manual, CSH Press, 1988; Ward et al., Nature 341 (1989) 544; Bird et al., Science 242 (1988) 423; Harlow, E. and Lane, D., Antibodies: A Laboratory Manual, Cold SpringHarbor Laboratory Press, Cold Spring Harbor, N.Y., 1999; WO94/02602, U.S. Pat. Nos. 5,223,409, 5,877,293, WO9101288.

The protein can also be detected using the techniques known to those skilled in the art of mass spectrometry, and such techniques are generally classified under proteomic analysis in order to detect specific signature sequences in a sample.

Alternatively, the inventive method can use any method for detecting the amount of Akt2 mRNA to determine the level of Akt2 mRNA in a tumor, wherein an elevated level of Akt2 mRNA in the tumor indicates that the tumor is a glucocorticoid resistant tumor. The detection methods described above includes various techniques capable of detecting nucleic acids in a sample, such as Northern blotting, selective hybridization, using a substrate coated with an oligonucleotide probe, such as a nucleic acid molecule array, a DNA chip and the like, by for example RT-PCR, quantitative PCR or PCR linked nucleic acid amplification and so on. These methods can include the use of a nucleic acid probe or primer capable of selectively or specifically detecting a nucleic acid target in a sample. For example, hybridization is known to those skilled in the art and can be performed with reference to standard conditions (Sambrook, Fritsch, Maniatis (1989) Molecular Cloning, Cold Spring Harbor Laboratory Press), for example, hybridization can be performed under high, moderate or low stringency conditions. Alternatively, amplification can be performed by those skilled in the art using various known methods, for example, PCR, LCR, transcription mediated amplification (TMA), strand displacement amplification (SDA), NASBA, and allele-specific oligonucleotides (ASO), allele-specific amplification, Southern blot, single-stranded conformation analysis (SSCA), in situ hybridization (e.g. FISH), gel shift assay, heteroduplex analysis, and the like.

In an embodiment of the present invention, the Akt2 detecting agent is a primer for detecting Akt2 mRNA or cDNA thereof, such as a sequence set forth in SEQ ID NO:3 or 4.

In another aspect, the present invention further provides use of the Akt2 detecting agent described herein for the preparation of a composition or kit for diagnosing a glucocorticoid resistant tumor.

As used herein, the term "kit" refers to a combination of the Akt2 detecting agent described herein with another item for a purpose of, including but not limited to, administering, diagnosing and evaluating the activity or property of, the Akt2 detecting agent. The kit optionally includes am instruction for use.

In another aspect, the present invention provides a method of treating a patient having a tumor, particularly a glucocorticoid resistant tumor characterized by elevated Akt2 expression, comprising administering to the patient a therapeutically effective amount of a glucocorticoid and an Akt2 inhibitor, for example, a pharmaceutical composition comprising an Akt2 inhibitor and a glucocorticoid. The administration can be performed by any suitable route, including but not limited to, parenteral route, for example, subcutaneous, oral or buccal or nasal mucosa. In an embodiment, the inventive method comprises administering to the patient a glucocorticoid (e.g. glucocorticoid) and an Akt2 inhibitor (e.g. CCT128930), at any suitable dose ratio, for example, a their molar concentration ratio may be, for example, 1:10 to 10:1, such as 1:10 to 5:1, 1:10 to 4:1, 1:10 to 3:1, 1:10 to 2:1, 1:10 to 1:1, 1:10 to 1:2, 1:10 to 1:3, 1:10 to 1:4 or 1:10 to 1:5. In an embodiment, the inventive method comprises administering to the patient a glucocorticoid (e.g. dexamethasone) and an Akt2 inhibitor (e.g. CCT128930), at a molar concentration ratio of 1:8.

As used herein, the "treating" a subject having a tumor refers to that the tumor of the subject is partially or completely eliminated, or remains stable without further progress after treatment. The treatment includes prevention, remedy and/or cure. The "prevention" refers to preventing the occurrence of a potential tumor and/or preventing the deterioration or progression of a tumor, including the reduction or elimination of one or more risk factors leading to tumor occurrence; as it is often impossible to determine whether a tumor has never occurred, prevention also includes reducing the risk of developing or having a tumor.

As used herein, the term "therapeutically effective amount" or "therapeutically effective dose" refers to an amount of an agent, compound or material in a dosage formulation that is at least sufficient to produce a therapeutic effect in a subject. For an Akt2 inhibitor of the present invention, a particular therapeutically effective dose can be initially estimated using various techniques known in the art. For example, in cell culture assays, an agent may be formulated in an animal model to produce a range of circulating concentrations comprising the IC50 as determined in cell culture. A dose range suitable for a human subject can be determined, for example, using data obtained from cell culture experiments and other animal studies. The dosage and regimen can be determined based on known dosages and regimens, if desired, extrapolated on the basis of Akt2 inhibitor properties and/or empirically determined based on various factors. The factors include subject's weight, general health, age, activity of the particular compound used, sex, diet, time of administration, speed of excretion, drug combination, severity and course of the disease, as well as patient's susceptibility to disease and physician's judgment. After the patient's conditions have improved, a maintenance dose of a compound or composition may be administered, and if desired, the dose, dosage form and frequency of administration or combination thereof may vary. The exact dose and regiment should be based on physician's judgment and patient's specific conditions.

In the present invention, an Akt2 inhibitor refers to a molecule capable of inhibiting the expression and/or activity of Akt2 at nucleic acid level and/or protein level. An Akt2 inhibitor available in the art can be used in the present invention. For example, an Akt2 inhibitor may be a small molecule compound, for example, a compound of the formula (I), (II), (Ill), (IV), (V) or (VI).

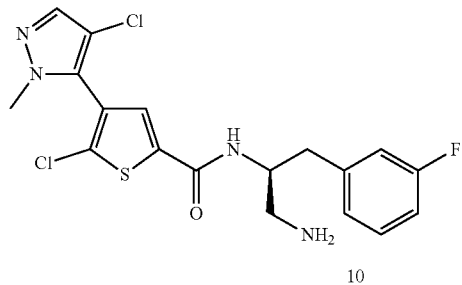

(I)

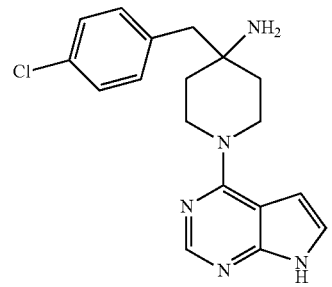

(II)

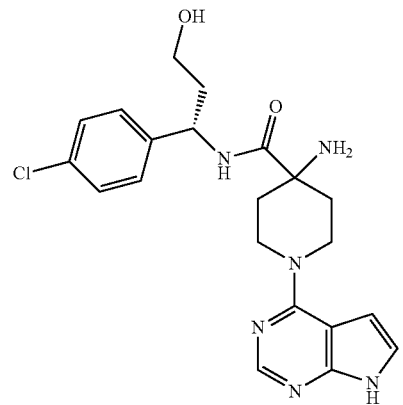

(III)

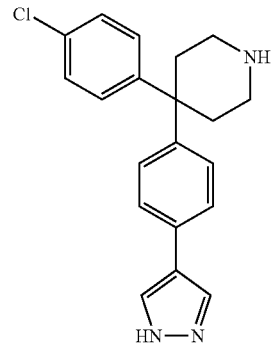

(IV)

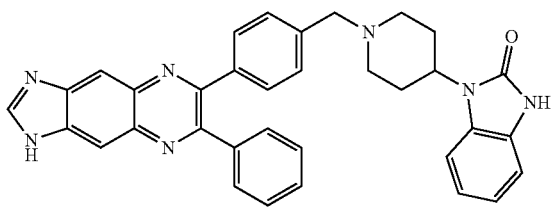

(V)

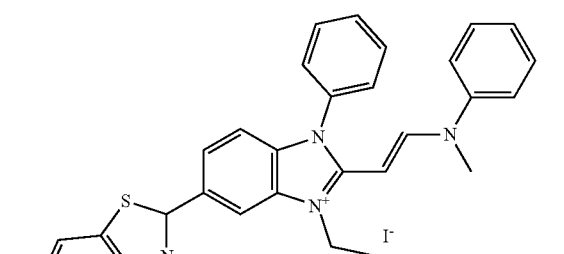

(VI)

Alternatively, an Akt2 inhibitor may be an mRNA interfering RNA molecule; or may be an antagonist of Akt2 protein, for example, a ligand, aptamer or antibody. In an embodiment, the Akt2 inhibitor is an antibody to Akt2 protein. In another embodiment, the Akt2 inhibitor is a double-stranded RNA (dsRNA), for example, a short interfering RNA (siRNA) or a short hairpin RNA (shRNA). The double-stranded RNA may be any type of RNA, including but not limited to mRNA, snRNA, microRNA, and tRNA. RNA interference (RNAi) is particularly useful for specifically inhibiting the production of specific RNA and/or proteins. The design and production of dsRNA molecules suitable for the present invention are within the skill of those skilled in the art, particularly with reference to Waterhouse et al. (1998), Smith et al. (2000), WO 99/32619, WO 99/53050, WO 99/49029 and WO 03/34815. Preferably siRNA molecule comprises a nucleotide sequence having about 19 to 23 contiguous nucleotides identical to the target mRNA. The term "shRNA" refers to a siRNA molecule in which fewer than about 50 nucleotides pair with the complementary sequence on the same RNA molecule, which sequence and complementary sequence are separated by an unpaired region of at least about 4 to 15 nucleotides (forming a single-chain loop on the stem structure produced by the two base-complementary regions). There are well-established siRNA design criteria (see, for example, Elbashire et al., 2001; Amarzguioui et al., 2004; Reynolds et al., 2004). For details, please refer to suppliers such as Ambion, Dharmacon, GenScript and OligoEngine. Once designed, the dsRNA used in the method of the present invention can be produced by any method known in the art, for example, by in vitro transcription, recombination or by synthetic means. The siRNA may be produced in vitro by using a recombinase (such as T7 RNA polymerase) and a DNA oligonucleotide template, or may be prepared in vivo, for example, in cultured cells. In a preferred embodiment, the nucleic acid molecule is produced synthetically.

In an embodiment of the present invention, the Akt2 inhibitor is an Akt2 selective or specific inhibitor. In the present invention, when used for inhibitor, the term "selective" and "specific" can be used interchangeably, meaning that the inhibitor has an inhibitory effect on the target only, or has a higher inhibitory effect on the target than on other compounds or molecules, for example, higher by at least about 1, 2, 3, 4, 5, 6, 7, 8, 9, 10, 20, 30, 40, 50, 100, 500, 1000, 10000 folds, and the like. For example, CCT128930 (Selleckchem) of the formula (II) is an effective ATP-competitive selective Akt2 inhibitor, which has an IC50 value of 6 nM in a cell-free assay and exhibits 28 folds of higher selectivity on Akt2 than closely related PKA kinase. In an embodiment of the present invention, the Akt2 inhibitor is a compound of the formula (II).

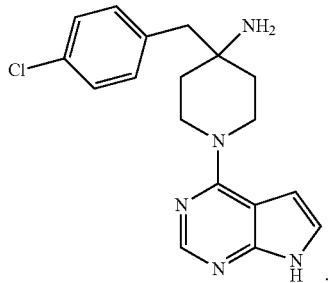

(II)

In another embodiment of the present invention, the Akt2 inhibitor is an interfering RNA molecule, for example, as set forth in SEQ ID NO: 7 or 8.

The Akt2 inhibitor can be administered in combination with another therapeutic agent or method, prior to, intermittently with, or after another therapeutic agent or method, including but not limited to another biological small molecule compound and surgery.

In another aspect, the present invention provides a pharmaceutical composition for treating a tumor, particularly a glucocorticoid resistant tumor characterized by elevated Akt2 expression, comprising the Akt2 inhibitor and glucocorticoid of the present invention and optionally a pharmaceutically acceptable carrier, excipient and/or diluent.

In an embodiment of the present invention, the Akt2 inhibitor and/or glucocorticoid may be formulated in a pharmaceutical composition. The pharmaceutical composition may be formulated for any suitable route of administration, for example, for oral, nasal, parenteral, intravenous, intramuscular, intradermal, subcutaneous, buccal, inhalant, intramucosal, or topical administration. For example, the pharmaceutical composition of the present invention may be in any pharmaceutical dosage form in the art, such as, a capsule, a pill, a tablet, a powder, a granule (e.g. bead, particulate or crystal), an aerosol, a spray, a foam, a solution, a dispersion, a tincture, a syrup, an elixir, a suspension, an ointment and a cream. The pharmaceutical composition may be formulated as a solid, liquid, gel or other forms. When the composition is formulated for oral administration, it may be formulated as a tablet or a capsule, for example, an enteric-coating tablet or an enteric-coating capsule.

In an embodiment, the Akt2 inhibitor and glucocorticoid may be formulated in the pharmaceutical composition of the present invention at any suitable ratio, for example, a molar concentration ratio of glucocorticoid to Akt2 inhibitor being 10:1 to 1:10, for example, 5:1, 4:1, 3:1, 2:1, 1:1, 1:2, 1:3, 1:4, or 1:5. In an embodiment, the molar ratio of glucocorticoid (such as dexamethasone) to Akt2 inhibitor (such as CCT128930) in the pharmaceutical composition of the present invention is 1:0.8.

The pharmaceutical composition of the present invention may comprises a pharmaceutically acceptable carrier, excipient and/or diluent, for example, including but not limited to lactose, sucrose, starch, talc, magnesium stearate, magnesium oxide, crystalline cellulose, methyl cellulose, carboxymethyl cellulose, gelatin, glycerin, sodium alginate, saline and water, and also an additive, for example, a filler, a binder, a wetting agent, a flow aid, a stabilizer, a preservative, an emulsifier and another solvent or solubilizer or substance for storage effect.

In another aspect, the present invention provides use of an Akt2 inhibitor according to the present invention for the preparation of a pharmaceutical composition for treating a tumor, particularly a glucocorticoid resistant tumor characterized by elevated Akt2 expression. In an embodiment, the pharmaceutical composition comprises an Akt2 inhibitor and a glucocorticoid and optionally a pharmaceutically acceptable carrier, excipient and/or diluent.

In an embodiment of the present invention, the tumor is a lymphocyte-derived tumor, such as lymphocytic leukemia, lymphoma such as B-cell lymphoma or T-cell lymphoma or myeloma. In an embodiment of the present invention, the tumor is a T cell-derived tumor, such as T-lymphocytic leukemia, T-cell lymphoma and myeloma. In an embodiment of the present invention, the lymphocytic leukemia is selected from the group consisting of acute lymphocytic leukemia and chronic lymphocytic leukemia. In an embodiment of the present invention, the lymphocytic leukemia is selected from the group consisting of B-cell lymphoma and T-cell lymphoma. In an embodiment of the present invention, the tumor is myeloma. In an embodiment of the present invention, the tumor is selected from the group consisting of Burkitt's lymphoma, T-lymphocytic leukemia such as acute T-lymphocytic leukemia and myeloma.

In an embodiment of the present invention, the B-cell lymphoma is selected from the group consisting of Hodgkin's lymphoma and non-Hodgkin's lymphoma, such as mucosa-associated lymphoid tissue lymphoma (MALT), small lymphocyte lymphoma/chronic lymphocytic leukemia, mantle cell lymphoma (MCL), diffuse large B-cell lymphoma and follicular lymphoma.

In an embodiment of the present invention, the T-cell lymphoma is selected from the group consisting of adult T-cell leukemia/lymphoma (ATL), peripheral T-cell lymphoma, atypical (PTCL-U) angioimmunoblastic T-cell lymphoma (AITL), angioimmunoblastic T cell lymphoma (AITL), subcutaneous panniculitis-like T-cell lymphoma (SCPTCL), cutaneous γδ T-cell lymphoma (CGD-TCL), hepatosplenic T-cell lymphoma (HSTCL), and enteropathy-type intestinal T-cell lymphoma (EITCL).

In an embodiment of the present invention, the tumor is acute T-Iymphocytic leukemia.

In the present invention, the glucocorticoid is any glucocorticoid-like drug that can be used by those skilled in the art for tumor treatment. In an embodiment of the present invention, the glucocorticoid is selected from the group consisting of dexamethasone, betamethasone, triamcinolone, triamcinolone acetonide, beclomethasone, prednisolone, prednisone, methylprednisolone, hydrocortisone, cortisone acetate, budesonide, beclomethasone dipropionate, ciclesonide, cortisone, methylprednisolone, clobetasol butyrate, fluocinonide, beclomethasone dipropionate, mometasone furoate, halcinonide, clobetasol propionate, halcinonide, halometasone, diflorasone diacetate and derivatives thereof. In an embodiment of the present invention, the glucocorticoid is dexamethasone or a derivative thereof.

As used herein, the range and amount may be expressed as "about" a particular value or range. The term "about" may also include a precise amount. Accordingly, the term "about 5%" refers to "about 5%" and "5%".

As used herein, the term "optional" or "optionally" means that the following described event or circumstance may or may not occur, and that the description includes an instance where the event or circumstance occurs and an instance where the event or circumstance does not occur. For example, an optional pharmaceutically acceptable carrier refers to the case including or not including the pharmaceutically acceptable carrier.

EXAMPLES

The present invention is further illustrated by the following examples, but any example or combinations thereof should not be construed as limiting the scope or implementation of the present invention. The scope of the present invention is defined by the appended claims, and the scope defined in the claims can be clearly understood by those skilled in the art in combination with the present description and common knowledge in the art. Without departing from the spirit and scope of the present invention, modifications or changes to the technical solution of the present invention can be made by those skilled in the art, and such modifications and changes are also included within the scope of the present invention.

Example 1: Correlation Between Dexamethasone Activity and Expression Level of the Proteins in the Akt/FoxO3a Pathway The CCRF-CEM cells (a human derived acute T-lymphocytic leukemia cell line, purchased from Shanghai Institute of Biochemistry and Cell Biology, Chinese Academy of Sciences) were inoculated at a density of $1 \times 10^5$ cells/ml in a cell culture dish (CORNING company) having RPMI 1640 complete medium (Gibco company) supplemented with 10% fetal bovine serum (FBS, Gibco company), and cultured in a 5% $CO_2$, 37° C. incubator (Thermo company) until reaching log growth phase; then, dexamethasone (DEX, Sangon Biotech (Shanghai) Co., Ltd.) was added to the dish in a final concentration of 0.1 µM or 1 µM, and cultured for further 48 h at 5% $CO_2$ and 37° C., and collecting the cells. The control group was not added with any reagents. All experiments were performed in triplicate.

Apoptosis was detected by Annexin V-FITC PI double staining method (flow cytometry kit (FITC, PI double staining), Sangon Biotech (Shanghai) Co., Ltd.)), and the collected cells were washed once with phosphate buffered saline (PBS) (135 mM NaCl, 2.7 mM KCl, 1.5 mM $KH_2PO_4$ and 8 mM $K_2HPO_4$, pH 7.2); the 4× binding buffer was diluted to a 1× binding buffer with deionized water, then the cells were resuspended with 195 ul of the 1× binding buffer at a cell density of $2-5 \times 10^5$/ml; 5 µl of Annexin V-FITC was added to the 195 µl of the cell resuspension and mixed, and incubated in dark at room temperature for 10 minutes; the cells were washed once with 200 µl of the 1× binding buffer, and then resuspended in 190 µl of the 1× binding buffer; 10 µl of propidium iodide (20 µg/ml) was added. A flow cytometry device (Beckman company) was used for detection, and the rate of apoptosis was analyzed using Summit software.

Protein detection by Western blot: in the examples of the present invention, Akt antibody (rabbit derived), phosphorylated Akt antibody (rabbit derived), FoxO3a antibody (rabbit derived), phosphorylated FoxO3a antibody (rabbit derived) and GAPDH antibody (rabbit derived) and secondary antibodies were all purchased from CST company. The cells were collected in a centrifuge tube and centrifuged at 1000 rpm, the supernatant was discarded and the cells were washed twice with PBS pre-cold at 4° C.; cell lysis buffer (150 mM NaCl, 1% NP-40, 0.1% SDS, 2 µg/ml Aprotinin, 2 µg/ml Leupeptin, 1 mM PMSF, 1.5 mM EDTA, 1 mM sodium vanadate) was added and the cells were lysed on ice for 40 minutes, the cell lysate was centrifuged at 20000 rpm, 4° C. for 15 minutes, and the supernatant was collected; a protein loading buffer for sodium dodecyl sulfate polyacrylamide (SDS-PAGE) gel electrophoresis (1.25 mL 1MTris-HCl (pH6.8), 0.5 g SDS, 25 mg BPB, 2.5 mL glycerol, 5 mL deionized water) was added, followed by boiling for 5 minutes to denature proteins; the loading buffer containing denatured proteins was applied to 10% SDS-PAGE for electrophoresis at 120 V, and then transferred to a PVDF membrane (Sangon Biotech (Shanghai) Co., Ltd.) at 130 V for 1.5 hours; after the membrane transfer was completed, the PVDF membrane was immediately rinsed with a Western washing solution (150 mmol/L NaCl, 50 mmol/L Tris-HCl (pH 7.5)) for 1-2 minutes; added with 5% non-fat milk powder (Shanghai Biotechnology Co., Ltd.), agitated gently and then blocked at room temperature for 60 minutes; a primary antibody diluted appropriately with 5% non-fat milk powder was added, and incubated overnight at room temperature with gentle agitating; the primary antibody was recovered and the membrane was washed three times with the washing solution for 5-10 minutes each; a horseradish peroxidase-labeled secondary antibody diluted appropriately with the Western washing solution was added, and incubated at room temperature for 1 hour with gentle agitating; the secondary antibody was recovered and the membrane was washed three times with the Western washing solution for 5-10 minutes each. An appropriate amount of developing solution (DAB 4 mg, 30% hydrogen peroxide 15 μL, 0.01 M Tris-Cl (pH 7.5) 5 mL) was dropped on the PVDF membrane, the image was detected using a bioluminescence image colorimeter and a gel imaging system (Thermo company), and the quantitative analysis of bands was performed using Image Lab software.

The data processing was performed using Excel and Stata software, data comparison was performed using t test, P<0.05 was considered statistically significant.

Results: as shown in FIG. 1A, for dexamethasone sensitive CCRF-CEM, the apoptosis was increased gradually along with the increased concentration of dexamethasone. As shown in FIG. 1B, as compared to the blank group, the expression of phosphorylated Akt in the cells treated with 0.1 μM dexamethasone was significantly down-regulated, and the phosphorylated Akt (Ser473)/total Akt was significantly decreased (p<0.05); accordingly, the expression of phosphorylated FoxO3a (Ser 253) was decreased, the total FoxO3a expression was increased, and the phosphorylated FoxO3a (Ser 253)/total FoxO3a protein was significantly down-regulated (p<0.05); and the above changes were more obvious along with increased concentration of dexamethasone.

Therefore, Akt is the major regulatory kinase for phosphorylation-inactivated FoxO3a in lymphocytes, and FoxO3a is an indispensable participant during dexamethasone-induced lymphocyte apoptosis.

Example 2: Abnormal Activation of Akt Pathway is the Mechanism by which Glucocorticoid Resistance Occurs in Lymphoid Tumor Cells CCRF-CEM cells were cultured in RPMI 1640 complete medium (Gibco company) containing 10% fetal bovine serum (FBS, Gibco company) and 1 μM dexamethasone (DEX, Sangon Biotech (Shanghai) Co., Ltd.) in an incubator (Thermo company) at 5% $CO_2$ and 37° C., and when 85%-90% confluence was reached, passaged by pipetting out ½-⅔ of the medium and adding fresh medium, and the 20th generation cells were treated with dexamethasone at concentrations of 1 μM, 25 μM, 50 μM and 100 μM for 48 hours, and the apoptosis detected by flow cytometry was not significantly increased, suggesting that a glucocorticoid-resistant cell line CEM-DR was obtained. Then, as described in Example 1, the CEM-DR cells were cultured to reach the logarithmic growth phase, and added with different concentrations of dexamethasone, and then the apoptosis was detected by Annexin V-FITC PI double staining and proteins were detected by Western blot. The Bim antibody (rabbit derived) was purchased from CST company.

Results: as shown in FIG. 1C, the apoptosis of cells treated with dexamethasone at concentrations of 25 μM, 50 μM, 100 μM was not significantly increased; but when treated with dexamethasone at a concentration of 200 μM, the apoptosis was significantly increased. As shown in FIG. 1D, as compared to CCRF-CEM cells, the total Akt expression was abnormally elevated in CEM-DR cells, the expression of phosphorylated FoxO3a (Ser253) was abnormally increased, and the expression of apoptosis protein Bim was down-regulated. CEM: CCRF-CEM cells.

By comparing with sensitive cell line CCRF-CEM, an abnormal increase in total Akt was found in CEM-DR cells.

Example 3: An Akt Inhibitor can Significantly Enhance the Sensitivity to a Glucocorticoid We compared the sensitization effect on glucocorticoid-induced tumor cell apoptosis of an Akt inhibitor Akt IV and other cell proliferation pathway inhibitors. The other cell proliferation pathway inhibitors include PI3K inhibitor LY294002, Notch1 pathway inhibitor dapt (abnormal Notch pathway may lead to thymocyte resistance to hormone-induced apoptosis), glycolysis inhibitor 2-DG (studies confirm that 2-DG can increase the sensitivity to glucocorticoids) and SGKs pathway (glucocorticoid-induced kinase) inhibitor GSK.

Methods: cells CCRF-CEM (human-derived acute T-lymphocytic leukemia cell line), Jurkat, Molt4 (human-derived acute T-lymphocytic leukemia cell line), Daudi, Raji (human-derived Burkitt's lymphoma cell line), L1210 (mouse-derived lymphoblastic leukemia cell line) and SP2/0 (mouse-derived myeloma cell line) were all purchased from Shanghai Institute of Biochemistry and Cell Biology, Chinese Academy of Sciences.

The cells were cultured in RPMI 1640 complete medium (Gibco company) containing 10% fetal bovine serum (FBS, Gibco company) in an incubator (Thermo company) at 5% $CO_2$ and 37° C. until reaching logarithmic growth phase, then different concentrations of inhibitors and/or dexamethasone/ethanol/DMSO were added to the culture medium, followed by further culturing (for addition of dexamethasone/ethanol/DMSO, for 48 hours, and for addition of inhibitor, for 24 hours), and apoptosis was detected by Annexin V-FITC PI double staining and proteins were detected by Western blot, as described in Example 1.

Figure 2:
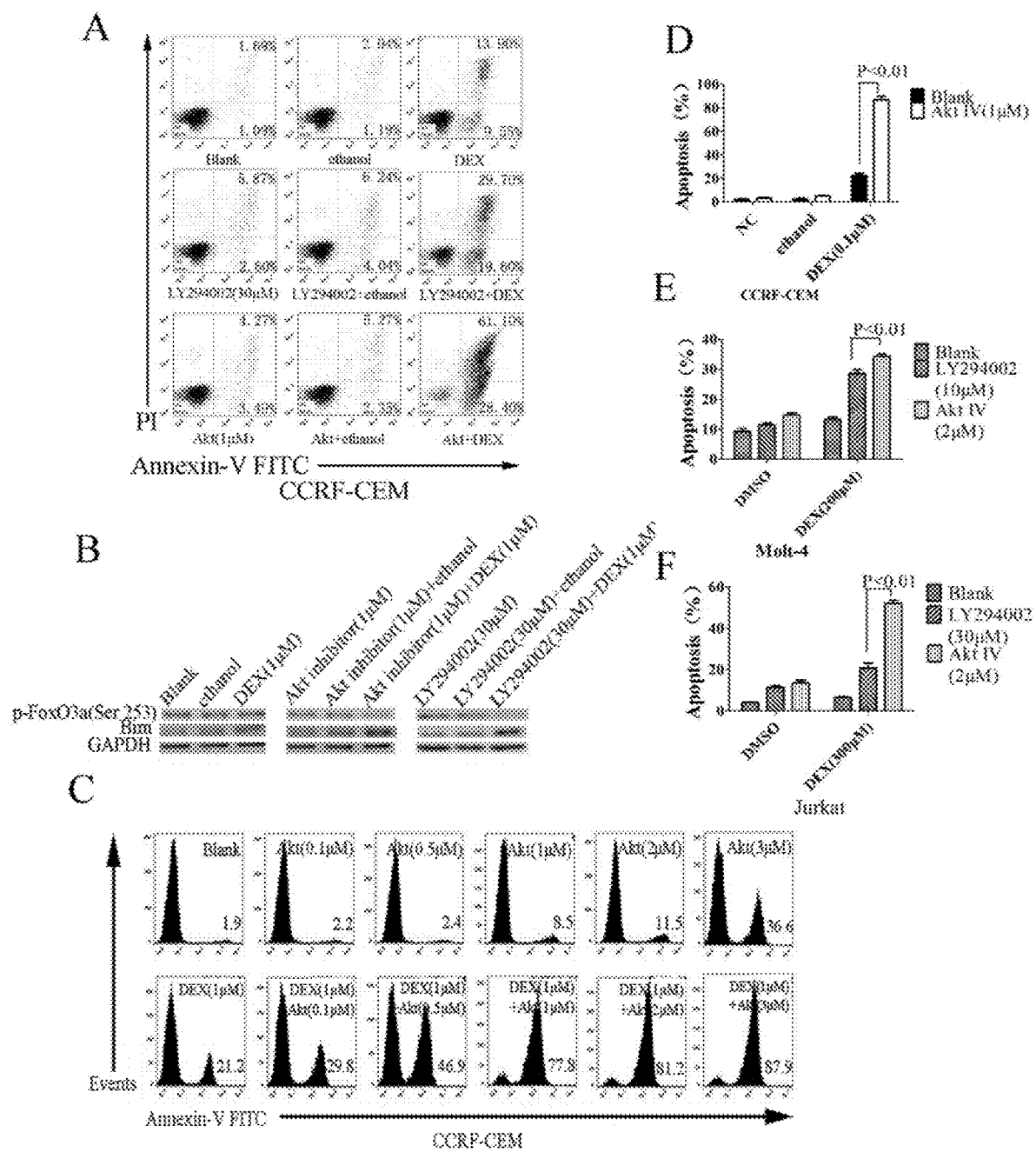
FIG. 2: the effect of a cell pathway inhibitor in combination with a glucocorticoid on apoptosis.
Figure 2:
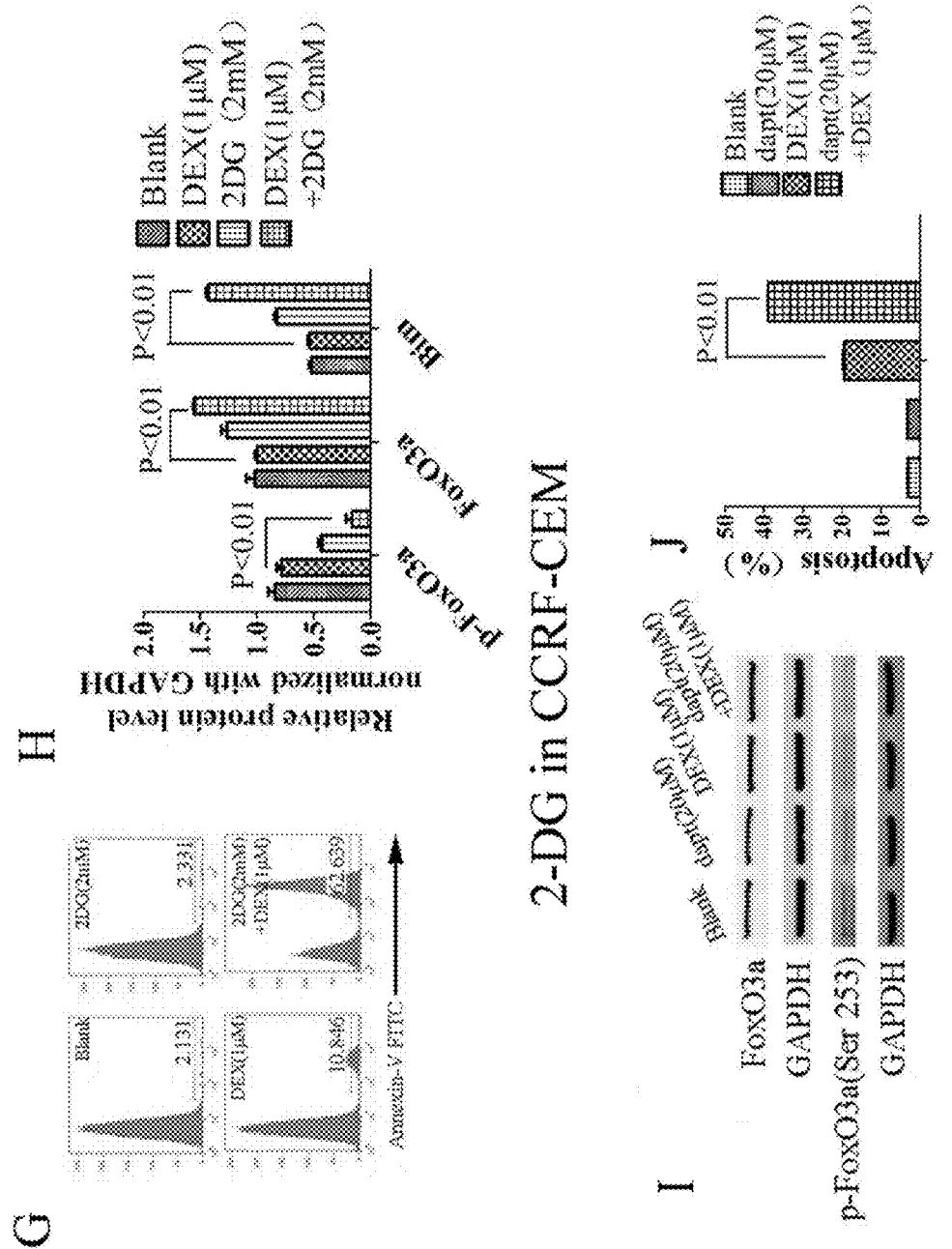
Figure 2:
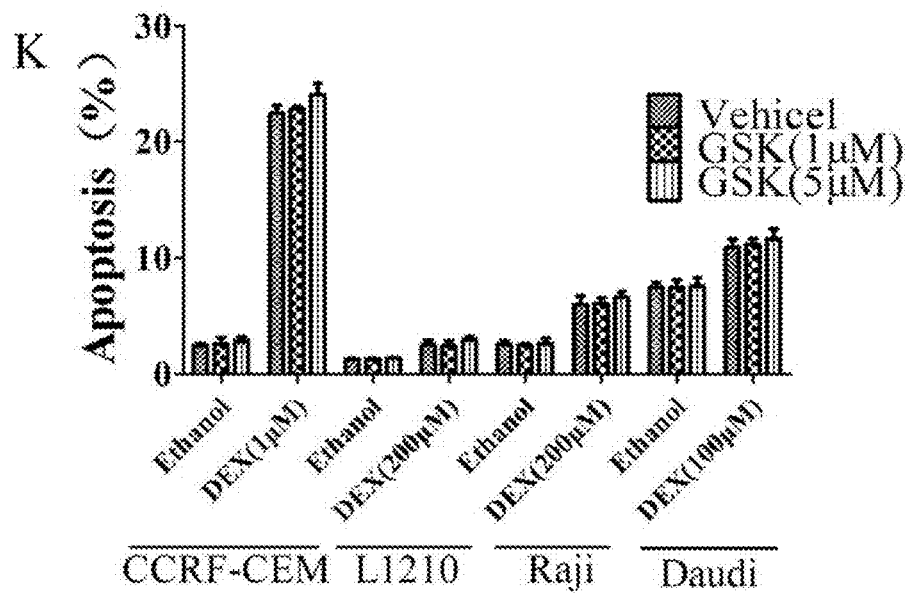
Figure 2:
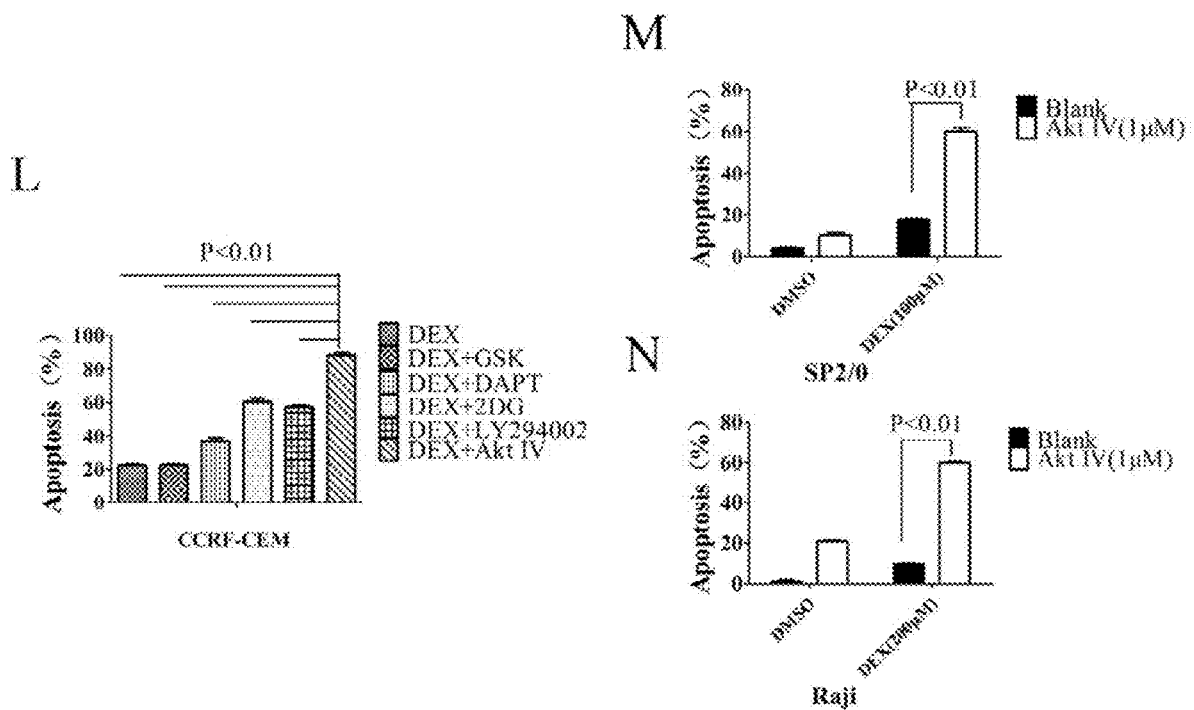

Results: as shown in FIG. 2A, as compared to dexamethasone alone, both Akt inhibitor Akt IV (Calbiochem company) and PI3K inhibitor LY294002 (Promega company) significantly increased the apoptosis of CCRF-CEM cells induced by dexamethasone (p<0.01). (Akt inhibitor: 1 μM; dexamethasone: 1 μM; LY294002: 30 μM; ethanol: 0.1%). As shown in FIG. 2B (ethanol: 0.1%), as compared to the only dexamethasone group, in the Akt inhibitor plus dexamethasone group and PI3K inhibitor LY294002 plus dexamethasone group, the expression of phosphorylated FoxO3a (Ser 253) was significantly down-regulated in CCRF-CEM cells, and the expression of the pro-apoptosis factor Bim was up-regulated. As shown in FIG. 2C, in the CCRF-CEM cell line, the Akt inhibitor at each concentration can increase the apoptosis induced by dexamethasone, and the apoptosis rate was increased along with the increased concentration of the Akt inhibitor. As shown in FIGS. 2E and 2F (DMSO: 0.1%), in highly glucocorticoid-resistant human-derived acute T-lymphocytic leukemia cell lines Molt4 and Jurkat, as compared to the only dexamethasone group, Akt inhibitor or PI3K inhibitor LY294002 in combination with dexamethasone significantly increased the apoptosis rate of cells (p<0.01), and the Akt inhibitor exhibited a better synergistic effect with dexamethasone than PI3K inhibitor LY294002 (p<0.01).

As shown in FIG. 2G, as compared to dexamethasone alone, glycolysis inhibitor 2-DG (Sigma company) significantly increased the apoptosis of CCRF-CEM cells induced by dexamethasone (p<0.01). As shown in FIG. 2H, as compared to dexamethasone alone, in the 2-DG plus dexamethasone group, the expression of phosphorylated FoxO3a was decreased, the total FoxO3a expression was increased, and the expression of pro-apoptosis factor Bim was significantly up-regulated (p<0.01).

As shown in FIG. 2J, as compared to dexamethasone alone, Notch1 pathway inhibitor dapt (Sigma company) significantly increased the apoptosis of CCRF-CEM cells induced by dexamethasone (p<0.01). As shown in FIG. 2I, as compared to dexamethasone alone, the expression of phosphorylated FoxO3a was significantly reduced in the dapt plus dexamethasone group.

As shown in FIG. 2K (ethanol: 0.1%), in the human-derived acute T-lymphatic leukemia cell line CCRF-CEM, mouse-derived T lymphoblastic leukemia cell line L1210, human-derived Burkitt's lymphoma cell line Raji and Daudi, there was no significant difference (p>0.05) in apoptosis rate between the dexamethasone group and GSK (Bioscience company) plus dexamethasone group, suggesting that the SGKs pathway inhibitor failed to synergize with dexamethasone to increase the apoptosis of tumor lymphocytes.

By comparing sensitization effect to glucocorticoids of the above cell proliferation pathway inhibitors, as shown in FIG. 2L, the Akt inhibitor was significantly superior to other cell proliferation pathway inhibitors, and exhibited the strongest effect of inducing apoptosis in combination with dexamethasone (p<0.01). As shown in FIGS. 2M and 2N (DMSO: 0.1%), in the murine-derived myeloma cell line SP2/0 and human-derived Burkitt's lymphoma cell line Raji, as compared to dexamethasone alone, the Akt inhibitor in combination with dexamethasone significantly increased the cell apoptosis (P<0.01), thereby increasing the sensitivity to glucocorticoids.

Example 4: Akt Inhibitor's Sensitization Effect to Glucocorticoid in Nude Mice Nude mice Balb/c (purchased from the animal research center of the Institute of Pharmacy, Fudan University) were bred in the specific pathogen free (SPF) animal room of the animal experimental center of the Institute of Pharmacy, Fudan University. The CCRF-CEM cells of logarithmic growth phase were collected and resuspended in serum-free RPMI 1640 medium at a cell density of about $1 \times 10^8$/ml. Four-week-old immunodeficient female nude mice were selected and treated by axillary subcutaneous injection of the cell suspension at 0.1 ml/mouse (about $1 \times 10^7$ cells/mouse). After four-week growth and tumor size reaching 300-500 $mm^3$, the mice were randomly grouped for experiment. The mice were intraperitoneally injected with dexamethasone at 0.1 mg/mouse and Akt inhibitor at 1.25 µg/mouse, once daily, for 7 days continuously. The overall survival time, tumor size and spleen cell apoptosis of the tumor-bearing mice were measured, and the pathological HE staining was carried out to tumors.

Figure 3:
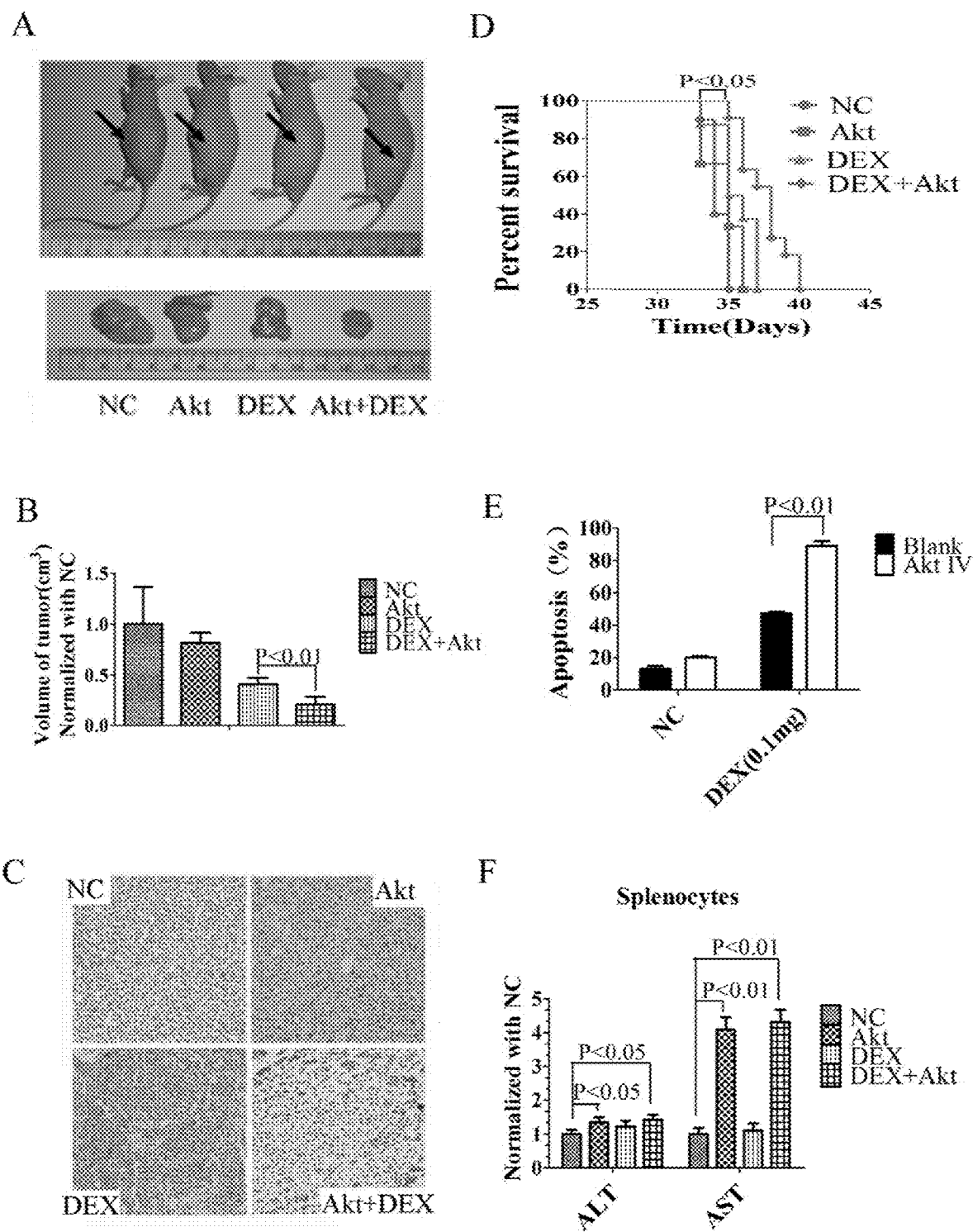
FIG. 3: the sensitization of an Akt inhibitor to glucocorticoids in nude mice.

Results: as shown in FIGS. 3A and 3B, as compared to the single dexamethasone group, the Akt inhibitor synergized with dexamethasone to reduce the size of subcutaneous tumor (p<0.01). As shown in FIG. 3D, as compared to the single dexamethasone group, the Akt inhibitor in combination with dexamethasone significantly increased the overall survival of tumor-bearing mice (p<0.05). Also, the mouse spleen lymphocytes were isolated for flow cytometry, and the results were shown in FIG. 3E. As compared to the single dexamethasone group, the apoptosis of spleen lymphocytes in the tumor-bearing mice was significantly increased (p<0.01).

The in vivo experiment in tumor-bearing mice confirmed again that the Akt inhibitor exhibited a significant sensitization effect to glucocorticoid.

Example 5: Akt Inhibitors have Severe Liver Toxicity

To further explore if there is toxicity of Akt inhibitor IV on liver, the levels of peripheral blood liver enzymes ALT and AST in mice were measured.

Methods: the levels of peripheral blood liver enzymes ALT and AST of the tumor-bearing mice prepared as described in Example 4 were measured after intraperitoneal injection of dexamethasone at 0.1 mg/mouse and Akt inhibitor at 1.25 µg/mouse once a day for 7 days continuously (National Advanced Medicine School Planning Teaching Material: Laboratory Animal Science (2nd Edition)).

Results: as shown in FIG. 3F, as compared to the normal saline group (NC), the levels of liver enzymes ALT and AST in the mice treated with the Akt inhibitor were significantly increased (p<0.05, 0.01). Accordingly, the Akt inhibitor exhibited obvious liver toxicity, which may affect the prospect of clinical application.

Example 6: Comparison of Synergistic Effect on Apoptosis of Lymphoid Tumor Cells Induced by Akt Inhibitors in Combination with Glucocorticoids As described in Example 3, the cells were cultured in RPMI 1640 complete medium containing 10% fetal bovine serum under 5% $CO_2$ and 37° C. until reaching logarithmic growth phase, and then dexamethasone and different concentrations of Akt inhibitor were added to the culture medium, followed by further culture (for addition of dexamethasone/DMSO, for 48 hours, and for addition of the inhibitor, for 24 hours), the apoptosis was detected by Annexin V-FITC PI double staining method and proteins were detected by Western blot as described in Example 1 as well as the cell viability was detected by CCK-8 method.

Cell viability detection by CCK-8 (Cell-Counting Kit (CCK-8) Kit, Dojindo Chemicals, Inc.): (1) the cells were seeded to the wells of a 96-well plate at a density of no more than $1 \times 10^4$ cell/well, with 5 replicates, each well was supplemented with 200 µl culture medium, different concentrations of drugs were added to respective wells according to the experimental requirements, followed by culture for 48 hours in an incubator under 5% $CO_2$ and 37° C.; (2) 10 µl of CCK-8 solution was added to each well while avoiding the formation of air bubbles in the wells, which may affect the readings of optical density (OD); (3) the plate was incubated in an incubator for 4 hours under 5% $CO_2$ and 37° C.; (4) the absorbance at 450 nm was read with a microplate reader; (5) the curve of cell viability was plotted: the cell viability was calculated according to the following equation and then a plot was generated, in which different drug concentrations or treatment time was set as x-axis and the cell survival as Y-axis;

Cell viability (%)=[$(As-Ab)/(Ac-Ab)$]×100%,

As: test wells (medium containing cells, CCK-8, toxic substances)

Ac: control wells (medium containing cells, CCK-8, free of toxic substances)

Ab: blank wells (medium free of cells and toxic substances, CCK-8).

Figure 4:
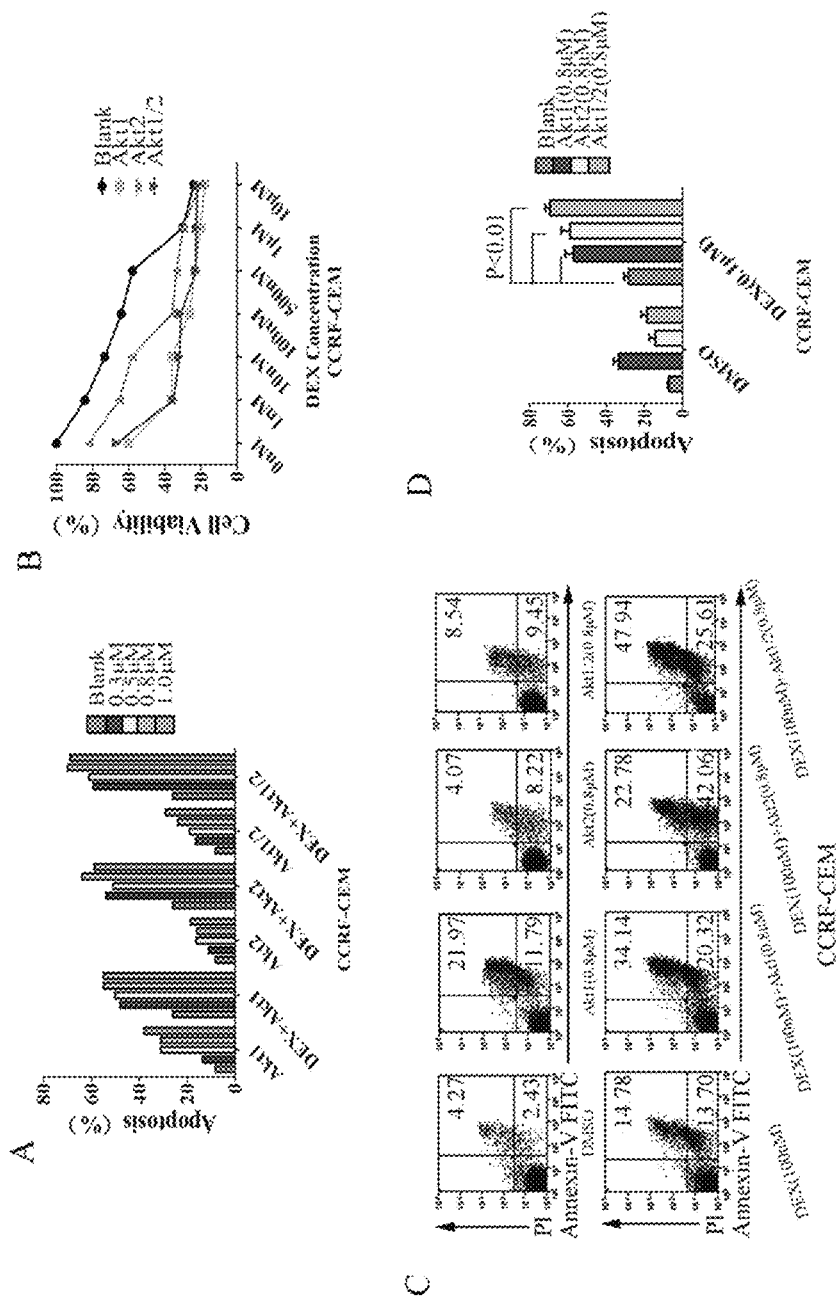
FIG. 4: the effect of an Akt inhibitor in combination with a glucocorticoid.
Figure 4:
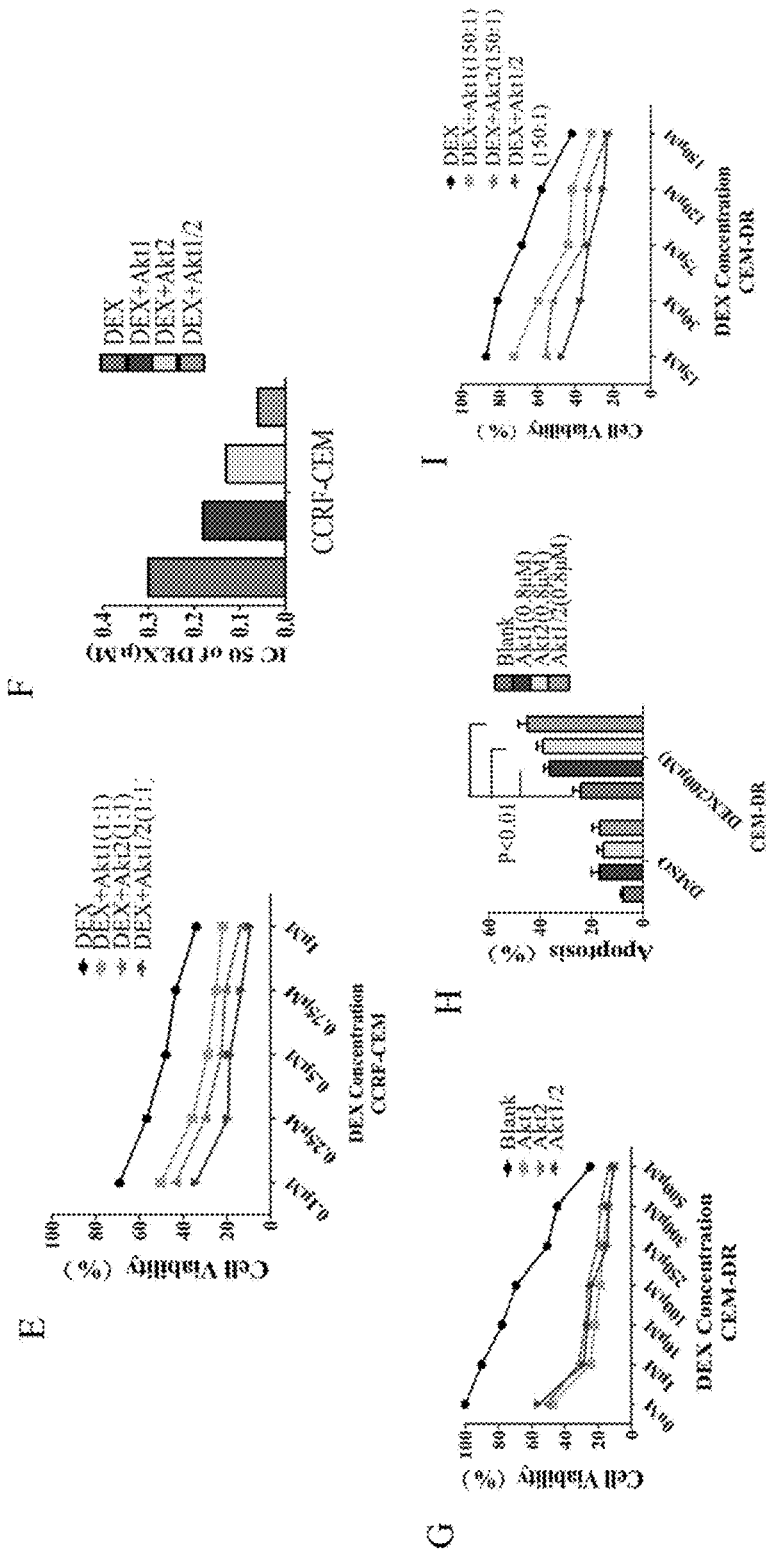
Figure 4:
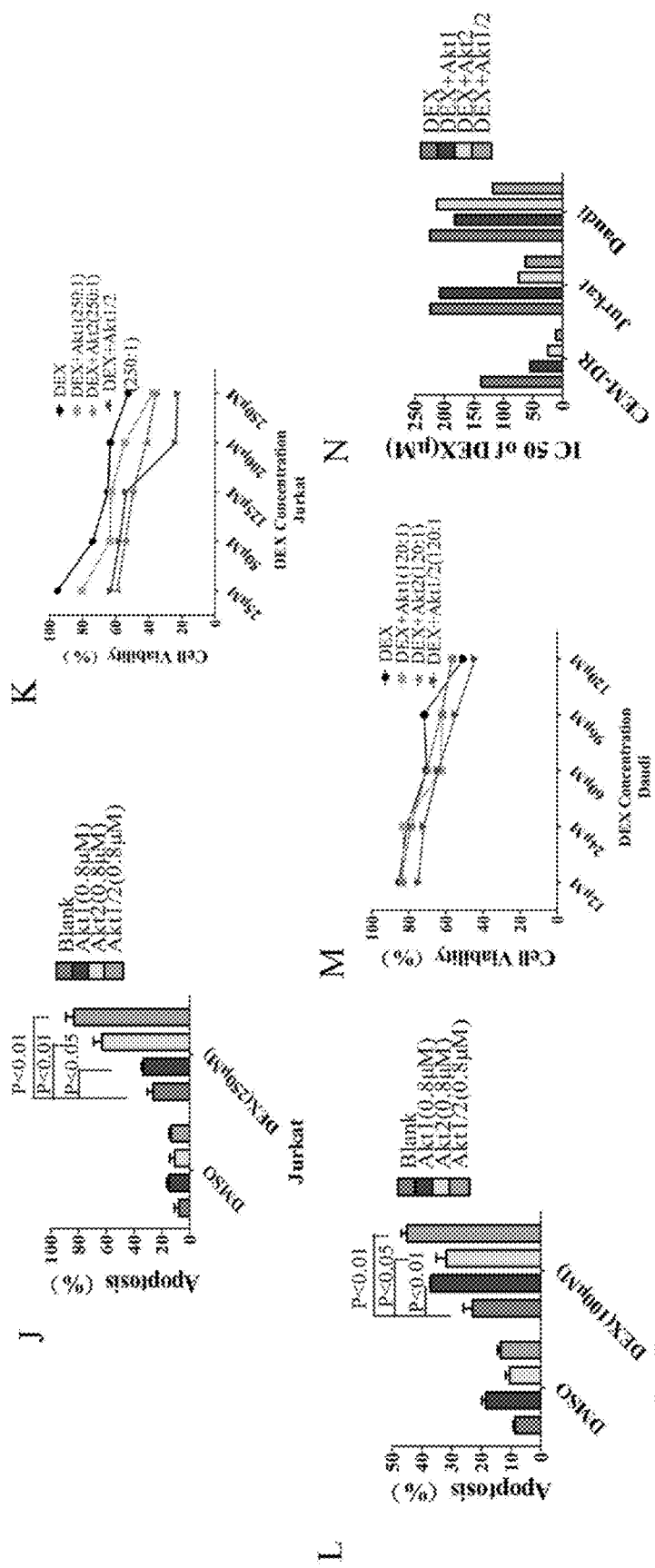

Results: using Akt1 inhibitor A-674563 (Selleckchem company) (inhibiting the phosphorylation activation of Akt1 downstream targets), Akt2 inhibitor CCT128930 (Selleckchem company) (inhibiting the phosphorylation activation of Akt2 downstream targets) and Akt1/2 co-inhibitor Akti-1/2 (Santa Cruz company) (inhibiting the autophosphorylation of both Akt1 and Akt2) for investigation, the CCRF-CEM cells were treated with 0.1 μM of dexamethasone in combination with 0.3 μM, 0.5 μM, 0.8 μM and 1 μM of Akt subtype inhibitors, and as shown in FIG. 4A, the results indicated that the effect on apoptosis was strongest with 0.1 μM of dexamethasone in combination with 0.8 μM of Akt subtype inhibitors. As shown in FIG. 4B, at different concentrations of dexamethasone (all of Akt1, Akt2, and Akt1/2 inhibitor at a concentration of 0.8 μM), Akt subtype inhibitors could significantly inhibit the viability of CCRF-CEM cells. As shown in FIGS. 4C and 4D (DMSO concentration: 0.1%), as compared to the single dexamethasone group, dexamethasone in combination with Akt inhibitors significantly increased the apoptosis of CCRF-CEM cells ($p<0.01$). As shown in FIGS. 4E and 4F, by applying Akt1, Akt2 and Akt1/2 inhibitors, the concentration of dexamethasone at which 50% viability of CCRF-CEM cells (IC50 value) was inhibited was lowered from original 0.3 μM to 0.18 μM, 0.13 μM and 0.03 μM, respectively.

In the cultured highly resistant cell line CEM-DR, as shown in FIG. 4G (all Akt1, Akt2 and Akt1/2 inhibitor at a concentration of 0.8 μM), all the Akt subtype inhibitors could significantly inhibit cell viability at different concentrations of dexamethasone. As shown in FIG. 4H (DMSO concentration: 0.1%), as compared to the single dexamethasone group, dexamethasone in combination with Akt subtype inhibitors significantly increased the apoptosis of CEM-DR cells ($p<0.01$). As shown in FIGS. 4I and 4N, by applying Akt1, Akt2 and Akt1/2 inhibitors, the concentration of dexamethasone at which 50% viability of CEM-DR cells (IC50 value) was inhibited was lowered from original 138 μM to 55 μM, 25 μM and 11 μM, respectively.

In the resistant human-derived T-lymphocytic leukemia cell line Jurkat, as shown in FIG. 4J (DMSO concentration: 0.1%), as compared to the single dexamethasone group, dexamethasone in combination with Akt1, Akt2, and Akt1/2 could significantly increase cell apoptosis ($p<0.05$, 0.01, 0.01); and the apoptosis of the DEX+Akt1 group was significantly lower than that of the DEX+Akt2 group ($p<0.01$). As shown in FIGS. 4K and 4N, by applying Akt1, Akt2 and Akt1/2 inhibitors, the concentration of dexamethasone at which 50% viability of Jurkat cells (IC50 value) was inhibited was lowered from original 224 μM to 208 μM, 74 μM and 63 μM, respectively.

In the resistant human-derived Burkitt's cell line Daudi, as shown in FIG. 4L (DMSO concentration: 0.1%), as compared to the single dexamethasone group, dexamethasone in combination with Akt1, Akt2, and Akt1/2 could significantly increase cell apoptosis ($p<0.05$, 0.01, 0.01); As shown in FIGS. 4M and 4N, by applying Akt1, Akt2 and Akt1/2 inhibitors, the concentration of dexamethasone at which 50% viability of Daudi cells (IC50 value) was inhibited was lowered from original 225 μM to 183 μM, 213 μM and 118 μM, respectively.

Accordingly, as compared to the single dexamethasone group, the Akt subtype inhibitors in combination with dexamethasone reduced the IC50 value of dexamethasone. Particularly, in T-lymphoid tumor cell lines (CCRF-CEM, CEM-DR, Jurkat cell lines), as compared to the single dexamethasone group, Akt subtype inhibitors significantly reduced the IC50 value of dexamethasone, exhibiting a remarkably synergistic effect with glucocorticoids, and the Akt2 and Akt1/2 inhibitors showed a better synergistic effect with glucocorticoids than the Akt1 inhibitor.

Example 7: Comparison of Combination Index of Akt Subtype Inhibitors in Combination with Glucocorticoids on the Inhibition of Lymphocyte Viability The inhibitory effect of two drugs (dexamethasone and an inhibitor) alone and in combination on various lymphocyte lines was observed by CCK-8 method (CCK-8 kit), and then the half-inhibitory concentration of each drug was calculated using the median effect equation, and the combination index (CI) of the two drugs used in combination was calculated using CompuSyn software.

(1) the lymphocytes of logarithmic growth phase were taken and made to a cell suspension of $5\times10^4$/mL, a blank control group (5 wells), a dexamethasone group (3 wells for each concentration, triplicates), a single inhibitor group (3 wells for each concentration, triplicates), a dexamethasone plus inhibitor group (3 wells for each combined concentration, triplicates) were prepared, 180 μL of the suspension was seeded to each well of a 96-well plate, and incubated for 24 hours in an incubator at 5% $CO_2$ and 37° C.

(2) two drugs were added to the 96-well plate at five different concentrations, and based on the drug resistance of cells, dexamethasone was prepared at five concentrations, and Akt1 inhibitor A-674563 (Selleckchem company), Akt2 inhibitor CCT128930 (Selleckchem company) and Akt1/2 inhibitor Akti-1/2 (Santa Cruz company) were prepared at five concentrations. Based on the drug resistance of cells, the ratio of two drugs was fixed. The dexamethasone group was cultured for 48 hours while the inhibitor group was cultured for 24 hours.

(3) 10 μl of CCK-8 was added to each well, and cultured for 2 hours, and the optical density (OD) was measured at 450 nm using an automatic microplate reader, and the proliferation inhibition rate of the drug on cell was calculated.

(4) the proliferation inhibition rate was calculated according to the following equation: cell proliferation inhibition rate=(1-average OD value in the test group/average OD value in the control group)×100%, and the effect of interaction between the two drugs was analyzed by Chou-Talalay combination index method.

Results: the value of CI of dexamethasone in combination with Akt subtype inhibitors was calculated using CompuSyn software, CI<1 indicating that the two drugs had synergistic effect, CI=1 indicating that the two drugs had an additive effect, and CI>1 indicating that the two drugs had an antagonistic effect. As shown in Table 1, in the T lymphoid tumor cells (CCRF-CEM, CEM-DR, Jurkat cells), Akt subtype inhibitors in combination with dexamethasone exhibited a highly synergistic effect, significantly inhibiting the viability of lymphoid tumor cells, and Akt2 and Akt1/2 inhibitors were significantly superior to the Akt1 inhibitor; In B lymphoma cells, the Akt1/2 inhibitor in combination with dexamethasone exhibited a moderate synergistic effect, the Akt2 inhibitor in combination with dexamethasone exhibited an additive effect, and the Akt1 inhibitor in combination with dexamethasone exhibited a low degree of synergistic effect.

TABLE 1 combination index of Akt subtype inhibitors and
dexamethasone in lymphoid tumor cell lines

| human-derived lymphoid tumor cells | DEX + Akt1 | | DEX + Akt2 | | DEX + Akt1/2 | |
|---|---|---|---|---|---|---|
| | CI | synergistic effect | CI | synergistic effect | CI | synergistic effect |
| CCRF-CEM | 0.59 | + | 0.27 | +++ | 0.15 | ++++ |
| CEM-DR | 0.87 | +− | 0.25 | +++ | 0.08 | ++++ |
| Jurkat | 1.2 | − | 0.38 | +++ | 0.39 | +++ |
| Daudi | 0.88 | +− | 0.97 | − | 0.73 | + |

Note:
DEX = dexamethasone
combination index CI < 1 indicating a synergistic effect of the two drugs, CI = 1 indicating an additive effect of the two drugs, CI > 1 indicating an antagonistic effect of the two drugs; $0.9 \leq CI \leq 1.1$ indicating an additive effect (−), $0.8 \leq CI < 0.9$ indicating a low degree of synergistic effect (+−), $0.6 \leq CI < 0.8$ indicating a moderate synergistic effect (+), $0.4 \leq CI < 0.6$ indicating a high synergistic effect (++), $0.2 \leq CI < 0.4$ indicating a strong synergistic effect (+++), CI < 0.2 indicating a super strong synergistic effect (++++).

Example 8: Mechanism of Akt2 Inhibitors for Sensitizing Glucocorticoid-Induced Apoptosis of Lymphocytes: Upregulating Intracellular FoxO3a/Bim Signaling Pathway Methods: CCRF-CEM cells were cultured in RPMI 1640 complete medium (Gibco company) containing 10% fetal bovine serum (FBS, Gibco company) in an incubator (Thermo company) at 5% $CO_2$ and 37° C. until reaching logarithmic growth phase, then DMSO, dexamethasone and different inhibitors (DMSO: 0.1%, dexamethasone: 0.1 μM, inhibitors: 0.8 μM) were added to the culture medium, and further cultured (for addition of dexamethasone or DMSO, for 48 hours, and for addition of inhibitors, for 24 hours), and the proteins were detected by Western blot, as described in Example 1.

Figure 5:
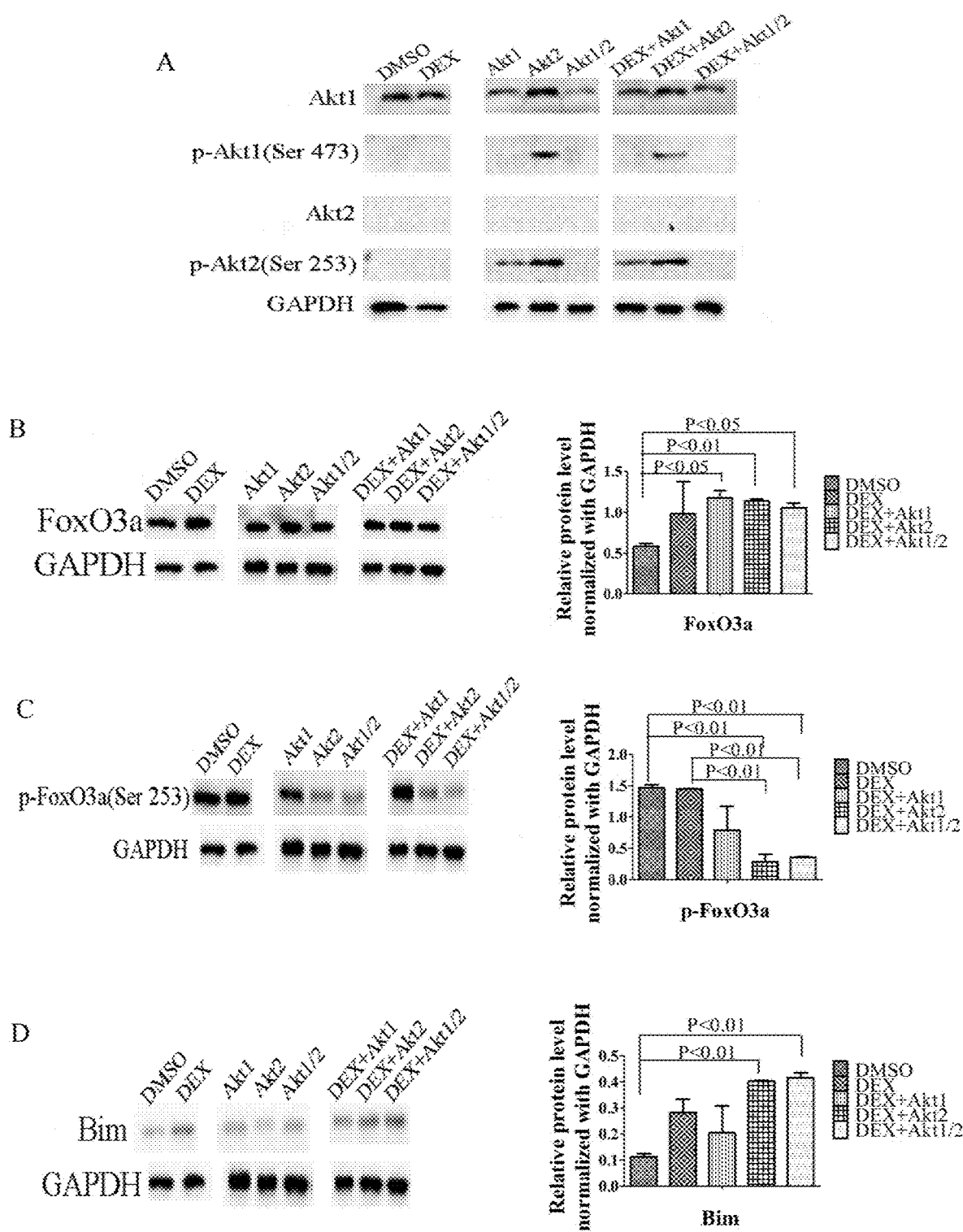
FIG. 5: the effect of an Akt subtype inhibitor in combination with a glucocorticoid on cell viability.
Figure 5:
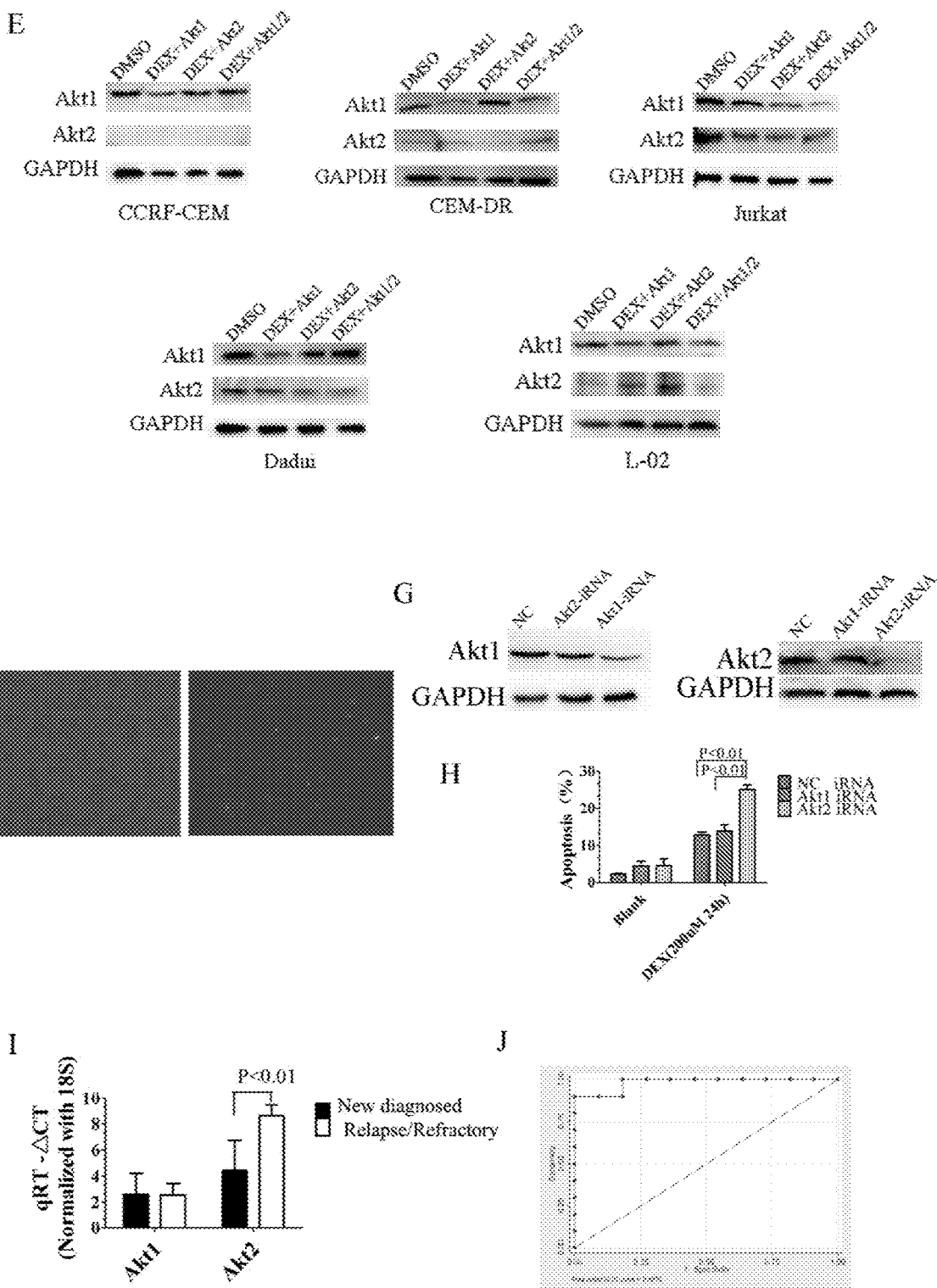

Results: as shown in FIG. 5A, in the CCRF-CEM cells treated with the Akt1 inhibitor, p-Akt1 was effectively inhibited, with a compensatory increase of p-Akt2. After pretreated with the Akt2 inhibitor, the expressions of p-Akt1 and p-Akt2 were increased in the cells. The Akt2 inhibitor does not inhibit the phosphorylation of Akt2, but inhibited the phosphorylation activation of downstream targets of Akt, leading to a compensatory increase of p-Akt1. The Akt1/2 inhibitor inhibited the phosphorylation activation of Akt itself, and the expression of p-Akt1 and p-Akt2 was reduced as compared to the DMSO group; however, as the expression of p-Akt1 and p-Akt2 was little in the DMSO group, the bands of p-Akt1 and p-Akt2 proteins in the Akt1/2 group and the DEX+Akt1/2 group did not appear.

As shown in FIG. 5B, as compared to the DMSO group, the level of total FoxO3a protein in the cells of the DEX+Akt1 group, DEX+Akt2 group and DEX+Akt1/2 group were significantly up-regulated (P<0.05, 0.01, 0.05); as compared to the DEX group, the levels of total FoxO3a protein in the cells of the DEX+Akt1 group, DEX+Akt2 group and DEX+Akt1/2 group were not significantly up-regulated (p>0.05). As shown in FIG. 5C, as compared to the DEX group, the levels of total FoxO3a proteins in the cells of the DEX+Akt2 group and DEX+Akt1/2 group were significantly down-regulated (p<0.01); there was no significant difference in the expression of intracellular p-FoxO3a protein between the DEX+Akt1 group and the DEX group (p>0.05). As shown in FIG. 5D, as compared to the DMSO group, the levels of pro-apoptotic protein Bim in the cells of the DEX+Akt2 group and DEX+Akt1/2 group were significantly up-regulated (p<0.01), and there was no significant difference in the expression of intracellular protein Bim between the DEX+Akt1 group and the DEX group (p>0.05).

By affecting the FoxO3a/Bim signaling pathway in the cells, the Akt2 inhibitor and Akt1/2 inhibitor significantly down-regulated the ratio of p-FoxO3a/total FoxO3a in cells, up-regulated the expression of pro-apoptotic protein Bim, and increased the apoptosis of lymphocytes induced by glucocorticoids, thereby playing a role in sensitization to glucocorticoids. The results of Western blot also confirmed that the Akt1 inhibitor did not significantly affect the FoxO3a/Bim signaling pathway in the cells, which explained why the Akt1 inhibitor had a relatively weak sensitization effect of lymphocytes to glucocorticoids.

Example 9: Relationship Between Akt2 Expression and Glucocorticoid Resistance in Lymphocytes Real-Time Quantitative PCR Assay
1. Sequence Design and Synthesis of mRNA Primers
The Akt1 and Akt2 primer sequences are as follows:

```
Akt1
                              (SEQ ID NO: 1)
sense strand primer: 5'-GCTGGACGATAGCTTGGA-3'

(SEQ ID NO: 2)
antisense primer: 5'-GATGACAGATAGCTGGTG-3'

Akt2
                              (SEQ ID NO: 3)
sense strand primer: 5'-GGCCCCTGATCAGACTCTA-3'

(SEQ ID NO: 4)
antisense primer: 5'-TCCTCAGTCGTGGAGGAGT-3'
```

2. RNA Extraction
Total RNA of the cells was extracted based on RNArose reagent instruction:

(1) $5 \times 10^6$ cells were added to 1 ml TRIZOL Reagent, followed by standing at room temperature for 5 minutes;

(2) 200 μl of chloroform was added (chloroform to RNArose Reagent was at a ratio of 1:5) and then agitated for 15 seconds, followed by standing at 15-30° C. for 2-3 minutes;

(3) the resulting mixture was centrifuged at 12000 rpm for 15 min at 4° C.;

(4) 400 μl of the upper aqueous phase was transferred to a new RNase-free centrifuge tube, and 40 μl of 3M sodium acetate solution (pH 5.5) and 1 ml of anhydrous ethanol were added, followed by precipitation at −20° C. for more than 4 hours to obtain total RNA;

(5) the product was centrifuged at 12,000 rpm for 10 min at 4° C., and the supernatant was discarded;

(6) the pellets were washed with 1000 μl (1:1) of 75% ethanol, followed by standing at −20° C. overnight or for the next step;

(7) the product was centrifuged at 12,000 rpm for 5 min at 4° C., the supernatant was discarded, and the pellets were dried at vacuum or in the air;

(8) RNA was dissolved in 30 μl of RNase-free water, agitated and slightly centrifuged for a few seconds, incubated at 55° C.–60° C. for 10 min, and then placed in a −70° C. freezer for use;

(9) a small amount of the above solution was taken for nucleic acid quantitative analysis using UV spectrophotometer, the values of OD260 and OD280 were measured to determine the concentration and purity of total RNA, the RNA concentration was adjusted, and the extract quality was observed by 1% agarose gel electrophoresis. The mRNA expression was detected by RT-PCR.

3. Reverse Transcription of mRNA into cDNA

| Total RNA | 1 μg |
|---|---|
| dNTP (0.5 mmol) | 10 mM |
| RT primer (2 pmol) | 10 μM |
| 65° C. 5 minutes | |
| 2 minutes on ice | |
| 5XFirst strand bull | 5 μl |
| DDT (5 mM) | 0.1M |
| RnaseOut (4U) | 40 U/μl |
| SuperscriptTMIIIreverse transcriptase | 100U | water (added up to 50 μl volume)
gently mixing
55° C. 60 minutes
70° C. 15 minutes
cDNA reaction product was obtained.

4. Detection of mRNA Abundance by Quantitative PCR Assay

The cDNA from above reverse transcription was diluted by 1:10 and used as a template to perform realtime PCR reaction using Power SYBR Green PCR Master Mix (ABI company). The reaction system was as follows.

| 2X mastermix | 1 μl |
|---|---|
| sense primer (100 μM) | 1 μl |
| antisense primer (100 μM) | 1 μl |
| cDNA template | 2 μl | water was added up to 20 μl of total volume, Realtime PCR analyzer 7500fast (ABI company) was used, the reaction conditions were as follows:

1) 94° C. 5 min
2) 94° C. 30 s
3) 55° C. 30 s
4) 72° C. 30 s
5) plate reading
6) to 2) repeating for 45 cycles
7) 72° C. 2 min
8) melting curve: 60° C. to 95° C., 90 s retention per 0.5° C., plate reading.

18 s rRNA was then used as normalized internal reference, and the results were analyzed using $2^{-\Delta\Delta ct}$ method.

Akt1, Akt2 RNA Small Interference Method: Cell Transfection

The transfected cells were selected and passaged for 3 to 5 passages after resuscitation, with Interferin™ as transfection reagent, and the transfection procedure was performed in accordance with the instruction of the transfection reagent. In short, the cells of logarithmic growth phase were plated at $2\times10^5$/well, the cells were replaced with fresh complete medium (free of antibiotics) during transfection, siRNA was diluted with Opti-MEM and added with an appropriate amount of INTERFERin™ and mixed, incubated at room temperature for 10 minutes prior to being added dropwise to the cells, and the cells were harvested at appropriate time. The cells were transfected with green fluorescein-labeled siRNA (FAM-siRNA) (siRNA at a final concentration of 20 μM, 1.25 μl/well), and the transfection efficiency was observed using a fluorescence microscope 24 hours later. The dexamethasone group was added 24 hours after transfection, followed by culture for further 24 hours, and then the cells were collected for observation; and the equal amount of anhydrous ethanol was added to the control group.

Akt1 siRNA:
(SEQ ID NO: 5)
GGCCCAACACCUUCAUCAUTT (SEQ ID NO: 6)
AUGAUGAAGGUGUUGGGCCTT

Akt2 siRNA:
(SEQ ID NO: 7)
GGUUCUUCCUCAGCAUCAATT (SEQ ID NO: 8)
UUGAUGCUGAGGAAGAACCTT

Results: as shown in FIG. 5E, the expression of Akt2 protein in the glucocorticoid-sensitive CCRF-CEM cells was extremely low, and the Akt2 protein band did not appear; in the highly resistant cell line CEM-DR derived from the CCRF-CEM cells, the expression of Akt2 protein in the cells was significantly increased as compared to the CCRF-CEM cells, and the Akt2 protein band appeared clearly; the expression of Akt2 protein in other two glucocorticoid resistant cell lines Jurkat and Daudi and normal liver cell line L-02 was significantly higher than that of the sensitive cell line CCRF-CEM.

As shown in FIGS. 5F and 5G, small interference RNAs were used to interfere with the expression of Akt1 and Akt2 in Jurkat cells, respectively. As shown in FIG. 5H, as compared to the dexamethasone group, the apoptosis of Jurkat cells with inhibited Akt2 expression induced by dexamethasone was significantly increased (p<0.01), and the apoptosis of Jurkat cells with inhibited Akt1 expression was not increased (p>0.05). NC: control group, transfected with empty plasmid without siRNA.

In 10 cases of initially treated patients and 11 cases of patients with refractory relapsed acute lymphoblastic leukemia (receiving a regime of chemotherapy including glucocorticoids, being refractory relapsed after an average of 7.2 treatment courses), the levels of Akt1 mRNA and Akt2 mRNA in myeloid lymphocytes were measured; and as shown in FIG. 5I, as compared to the initial treatment group, the expression of Akt2 mRNA in the refractory relapsed group was significantly elevated (p<0.01), and there was no significant difference in the expression of Akt1 mRNA (p>0.05). According to the ROC curve analysis, as shown in FIG. 5J, Akt2 was used as a marker for detecting the degree of glucocorticoid resistance in patients, the area under the ROC curve was 0.9818, the best judgment threshold was 16.39, the diagnostic sensitivity was 90%, and the specificity was 100%.

Accordingly, we have found that the overexpression of Akt2 in the cells may be an important mechanism causing glucocorticoid resistance in lymphocytes: by inactivating FoxO3a through phosphorylation, up-regulating the p-FoxO3a/total FoxO3a ratio and down-regulating the expression of pro-apoptotic factor Bim, the up-regulated Akt2 inhibited the intracellular FoxO3a/Bim signaling pathway, leading to the development of glucocorticoid resistance.

Example 10: Comparison of Toxic Effect of Akt1 and Akt2 Inhibitors on Liver Cells L-02 human-derived healthy liver cell line was purchased from Shanghai Institute of Biochemistry and Cell Biology, Chinese Academy of Sciences. Nude mice were purchased from the animal research center of the Institute of Pharmacy, Fudan University and bred in the specific pathogen free (SPF) animal room of the animal experimental center of the Institute of Pharmacy, Fudan University.

CCK-8 assay was performed as described in Examples 6 and 7, and Western blot was performed as described in Examples 1 and 2.

The CCRF-CEM cells of logarithmic growth phase were collected and resuspended in serum-free RPMI 1640 medium at a cell density of about $1\times10^8$/ml. Four-week-old immunodeficient female nude mice were selected and treated by axillary subcutaneous injection of the cell suspension at an amount of 0.1 ml/mouse (about $1\times10^7$ cells/mouse). After four-week growth and tumor size reaching 300-500 mm$^3$, the mice were randomly grouped for experiment. The mice were intraperitoneally injected with dexamethasone at 0.1 mg/mouse and the Akt1, Akt2 or Akt1/2 inhibitor at 1.25 µg/mouse, once a day, for 7 days continuously. On day 8, the blood samples were taken from the orbit, and then sent to Shanghai Animal Testing Center for peripheral blood test.

Results: the experimental results of the L02 liver cell line were shown in FIG. 6A-6F, with DMSO: 0.1%; DEX: 0.1 µM; Akt1 inhibitor, Akt2 inhibitor and Akt1/2 inhibitor: 0.8 µM.

Figure 6:
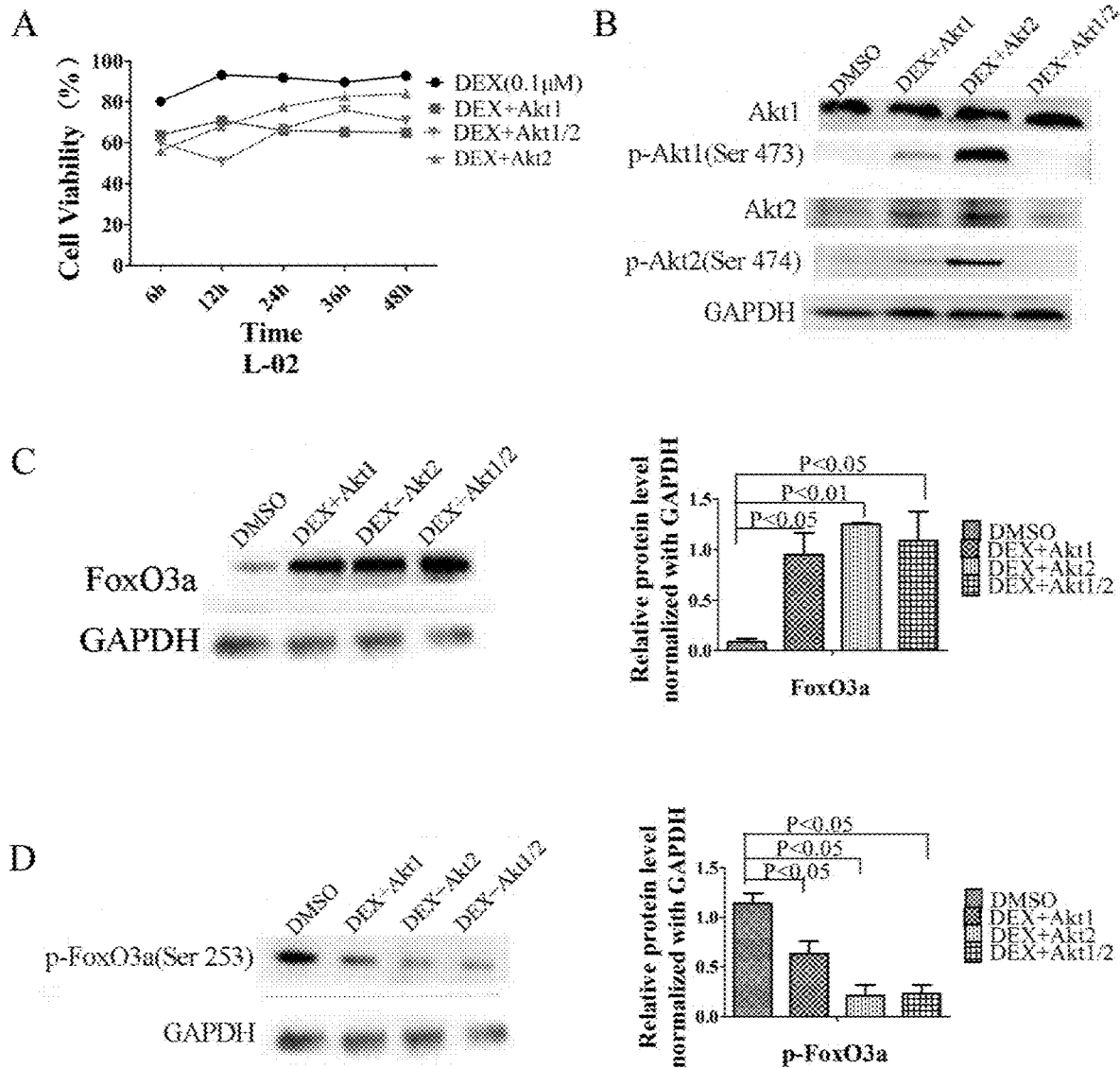
FIG. 6: the effect of Akt1 and Akt2 inhibitors in combination with dexamethasone on healthy liver cells.
Figure 6:
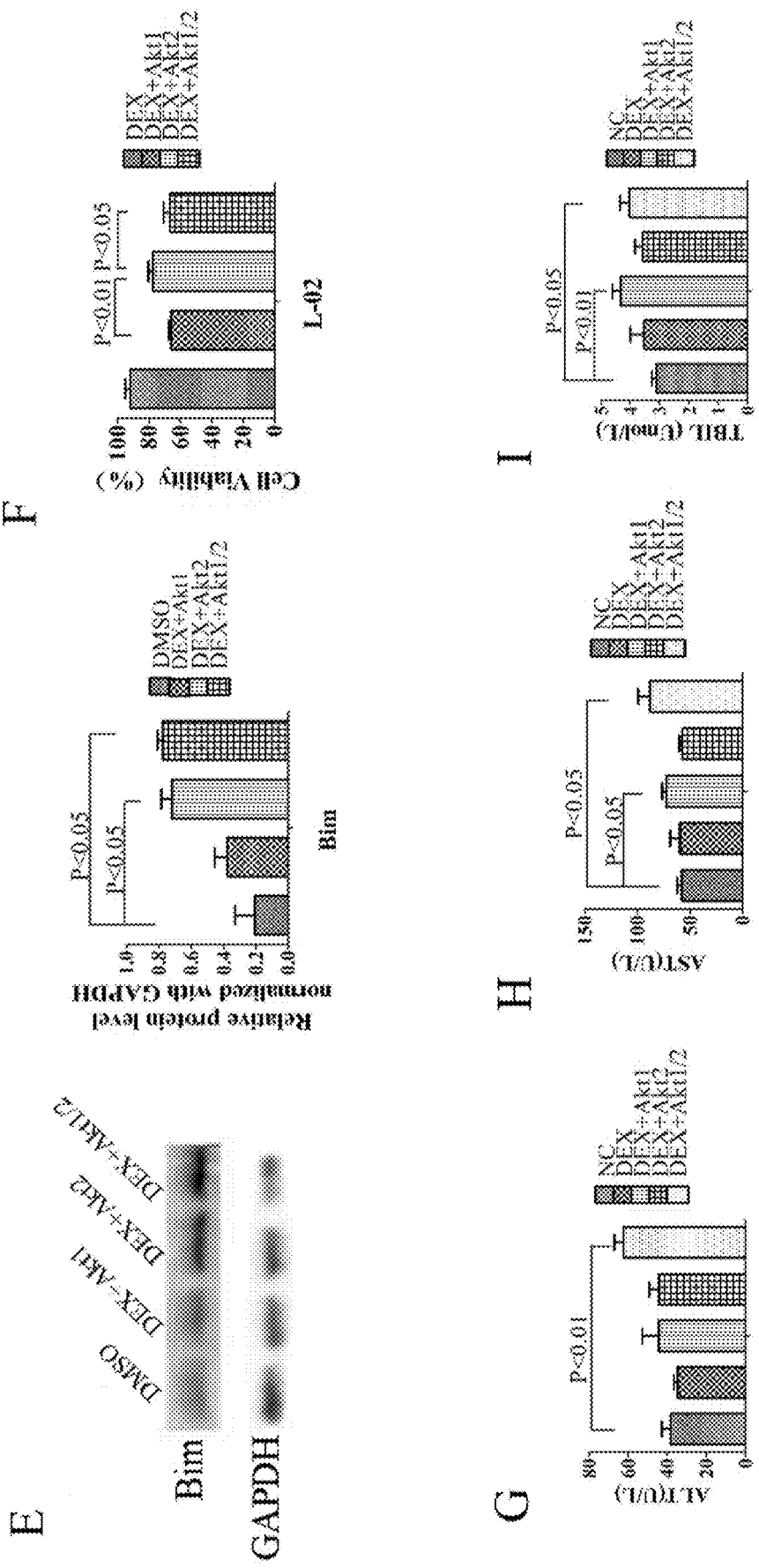
Figure 6:
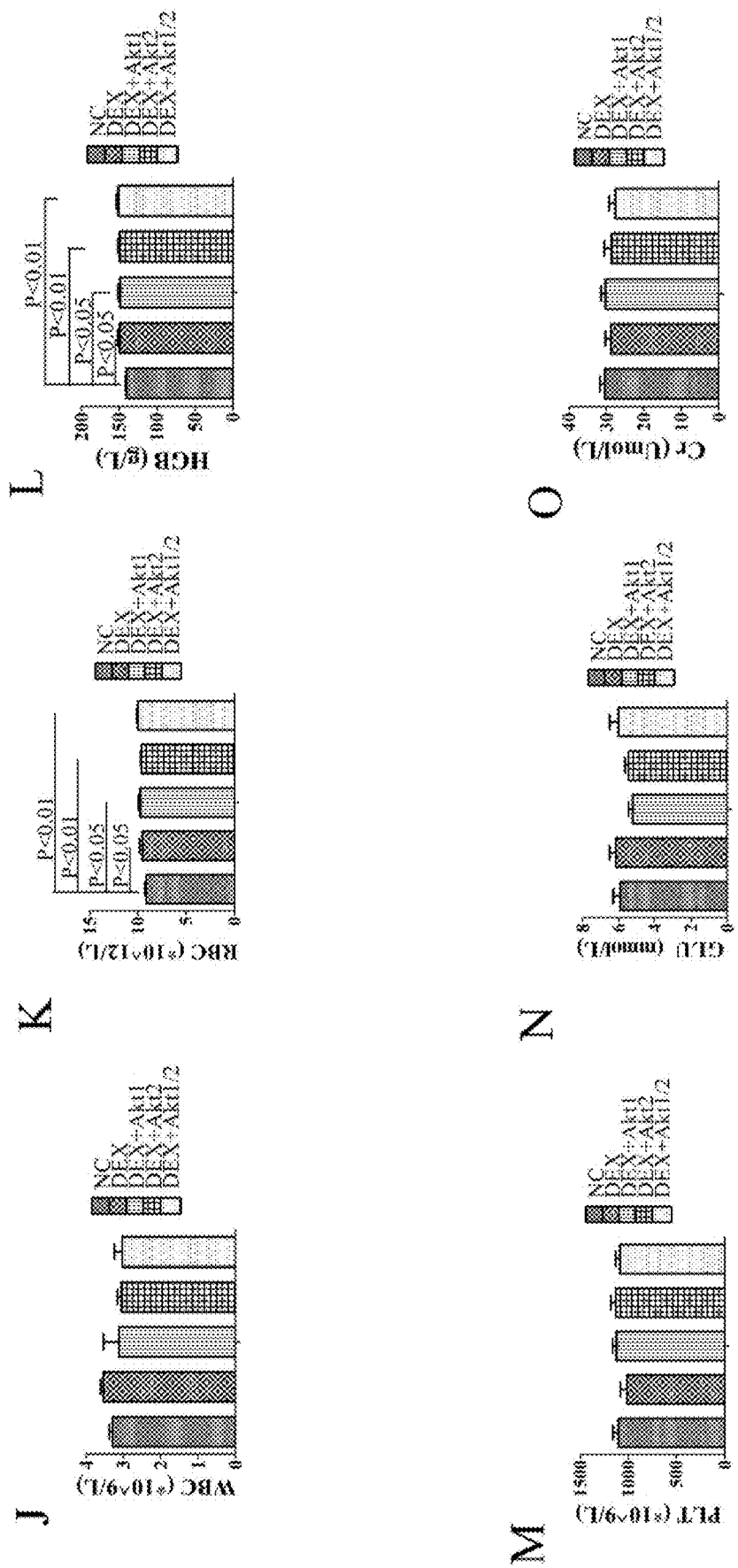

As shown in FIG. 6A, dexamethasone had no damage to liver cells; the Akt1 inhibitor exhibited the most serious damage to the liver cells, and liver cell activity did not recover within 48-hour after administration; the Akt1/2 inhibitor exhibited a certain damage to the liver cells, and the liver cell activity was reduced down to 50.5% after 12 hours of administration, and the liver cell activity gradually recovered after 24 hours of administration; the Akt2 inhibitor exhibited the least damage to the liver cells, and the liver cell activity was reduced to 56.1% after six hours of administration, and the liver cell activity gradually recovered after 6 hours of administration, and after 24 hours of administration, the liver cell activity in this group was always higher than that of both the Akt1 inhibitor group and Akt1/2 inhibitor group.

As shown in FIG. 6B, after the L-02 cells were pretreated with the Akt1 inhibitor or Akt2 inhibitor, the expressions of p-Akt1 and p-Akt2 in the cells were correspondingly increased. As shown in FIG. 6C, as compared to the DMSO group, the levels of total FoxO3a protein in the cells of the DEX+Akt1, DEX+Akt2 and DEX+Akt1/2 groups were all significantly up-regulated (p<0.05, 0.01, 0.05). As shown in FIG. 6D, as compared to the DMSO group, the expressions of total FoxO3a protein in the cells of the DEX+Akt1, DEX+Akt2 and DEX+Akt1/2 groups were significantly down-regulated (p<0.05, 0.05, 0.05). As shown in FIG. 6E, as compared to the DMSO group, the expressions of pro-apoptotic protein Bim in the cells of the DEX+Akt2 and DEX+Akt1/2 groups were significantly up-regulated (p<0.05), and there was no significant difference in the expression of the intracellular protein Bim between the DEX+Akt1 and the DMSO groups (p>0.05). After the liver cell line L-02 was treated with an Akt subtype inhibitor for 24 hours, as shown in FIG. 6F, the cell viability of the DEX+Akt2 group was significantly higher than that of the DEX+Akt1 and DEX+Akt1/2 groups (p<0.01, 0.05). The above results suggested that after 24-hour of administration, although the Akt2 signaling in the liver cells was inhibited, dexamethasone can induce the expression of Bim by FoxO3a to cause partial apoptosis, while the Akt1 inhibitor and Akt1/2 inhibitor were stronger to the Akt2 inhibitor in inhibiting the liver cell activity, which may be caused by the inhibition of the mTOR pathway related to cell growth and proliferation due to Akt1 target inhibition, producing a greater effect on liver cell activity. The inhibition of the FoxO3a/Bim pathway that is the main target of Akt2 may also regulate glucocorticoid-induced liver cell apoptosis, producing a certain effect on liver cell activity, however, the effect of this process on liver cell activity was more slight than that resulting from the inhibition of Akt1/mTOR pathway, and the compensatory increased p-Akt1 may enhance the Akt1/mTOR signaling pathway to enable the recovery of liver cell activity.

The toxicity of Akt subtype inhibitors in nude mice was investigated, as shown in FIG. 6G, as compared to the NC group, the level of ALT in the mice treated with the Akt1/2 inhibitor was significantly increased (p<0.01). As shown in FIG. 6H, as compared to the NC group, the level of AST in the mice treated with the Akt1 and Akt1/2 inhibitors was significantly increased (p<0.05). As shown in FIG. 6I, as compared to the NC group, the level of TBIL in the mice treated with the Akt1 and Akt1/2 inhibitors was significantly increased (p<0.01, 0.05). As shown in FIGS. 6J and 6M-6O, as compared to the NC group, there was no significant difference of peripheral blood leukocyte, platelet, creatinine and blood glucose levels in the DEX, DEX+Akt1, DEX+Akt2 and DEX+Akt1/2 groups (p>0.05). As shown in FIG. 6K-6L, as compared to the NC group, the levels of peripheral blood RBC and HGB in the DEX, DEX+Akt1, DEX+Akt2 and DEX+Akt1/2 groups were significantly increased, which may be caused by the migration of red blood cells from the reserve pool to the circulation pool due to the stimulation of glucocorticoids, leading to the increased peripheral blood red blood cell counting. NC: control group, injected with normal saline.

Figure 8:
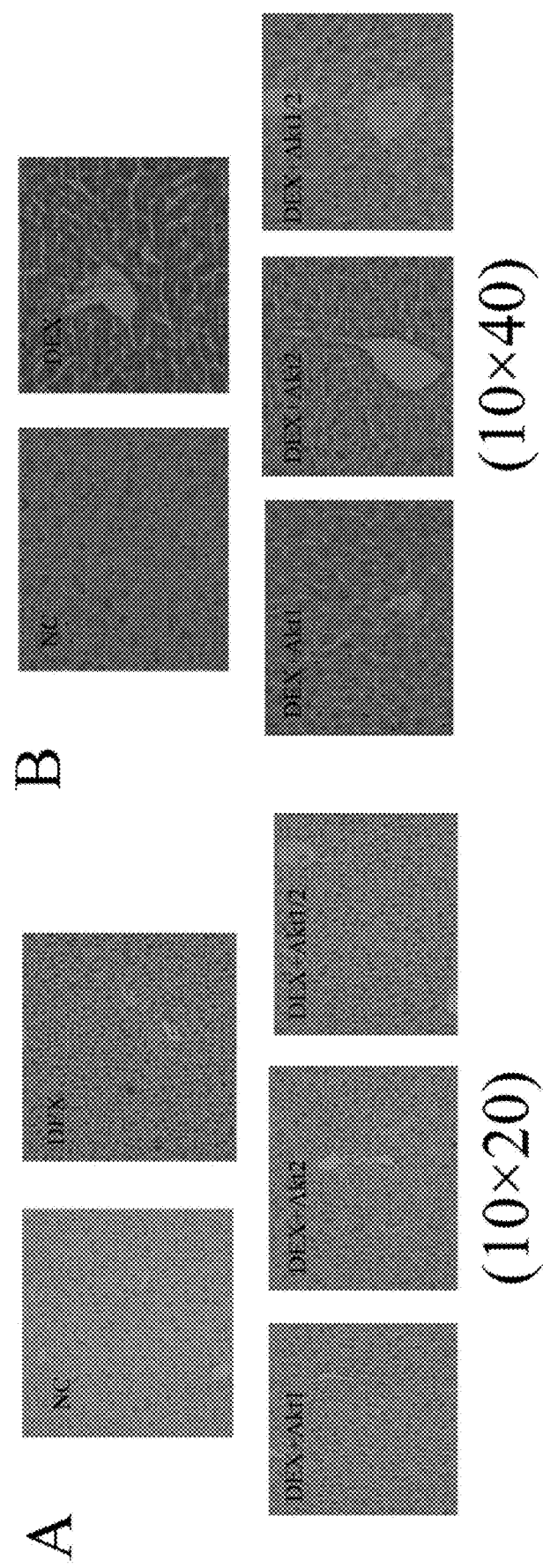
FIG. 8: the pathological sections of organs of nude mice.
Figure 8:
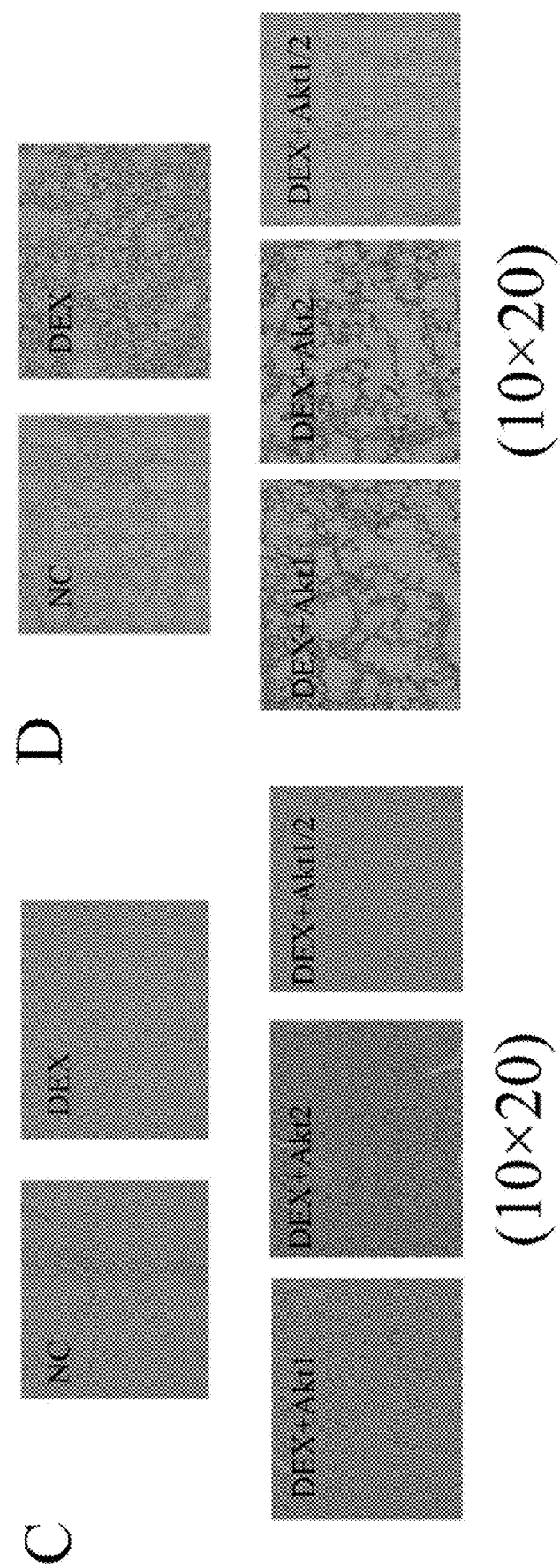
Figure 8:
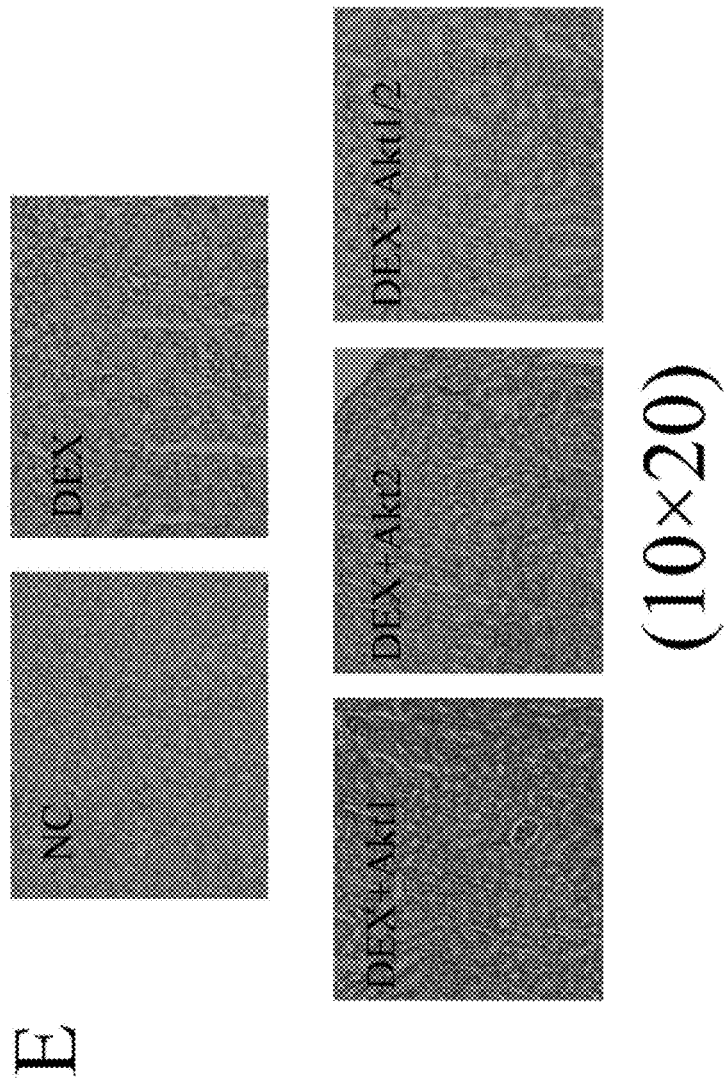

Also, the pathological specimens of important organs of tumor-bearing mice in each group were prepared, including the heart, lung, kidney and liver, followed by pathological section and HE staining. As shown in FIGS. 8A and 8B, the liver cells of tumor-bearing mice in each group appeared normal morphology with no degeneration or necrosis, no proliferation of fibrous tissue was observed, and no inflammatory cell infiltration was observed in the liver intercellular matrix. As shown in FIG. 8C, the myocardial cells of tumor-bearing mice in each group appeared normal morphology, and no inflammatory cell infiltration was observed in the myocardial intercellular matrix. As shown in FIG. 8D, the tumor-bearing mice in each group appeared good alveolar filling and normal alveolar cell morphology, with no obvious bleeding or exudation in the alveolar cavity. As shown in FIG. 8E, the tumor-bearing mice in each group appeared normal glomerular and tubular structures, with no mesangial cell proliferation, and no inflammatory cell infiltration was observed in renal interstitial substances. The above pathological results suggested that although the Akt1 and Akt1/2 subtype inhibitors caused certain damage to the liver cells, resulting in the increased levels of peripheral blood liver enzymes and total bilirubin in the mice, the inhibitors did not cause morphological changes of the liver tissues within 7-day administration.

Example 11: In Vivo Validation of Glucocorticoid Sensitization Effect of Akt Subtype Inhibitors in Tumor-Bearing Mice The CCRF-CEM cells of logarithmic growth phase were collected and resuspended in serum-free RPM11640 medium at a cell density of about $1\times10^8$/ml. Four-week-old immunodeficient female nude mice were selected and treated by axillary subcutaneous injection of the cell suspension at 0.1 ml/mouse (about 1×10$^7$ cells/mouse), allowed to grow for four weeks to reach a tumor size of 300-500 mm$^3$, and then randomly grouped for experiment. The mice were intraperitoneally injected with dexamethasone at 0.1 mg/mouse and the Akt1, Akt2 or Akt1/2 inhibitor at 1.25 μg/mouse, once a day, for 7 days continuously. The overall survival, tumor size and spleen size of the tumor-bearing mice were measured, the pathological sections of tumor were for HE and Ki-67 staining, and the pathological sections of spleen were for HE, CD3, and TdT staining.

Figure 7:
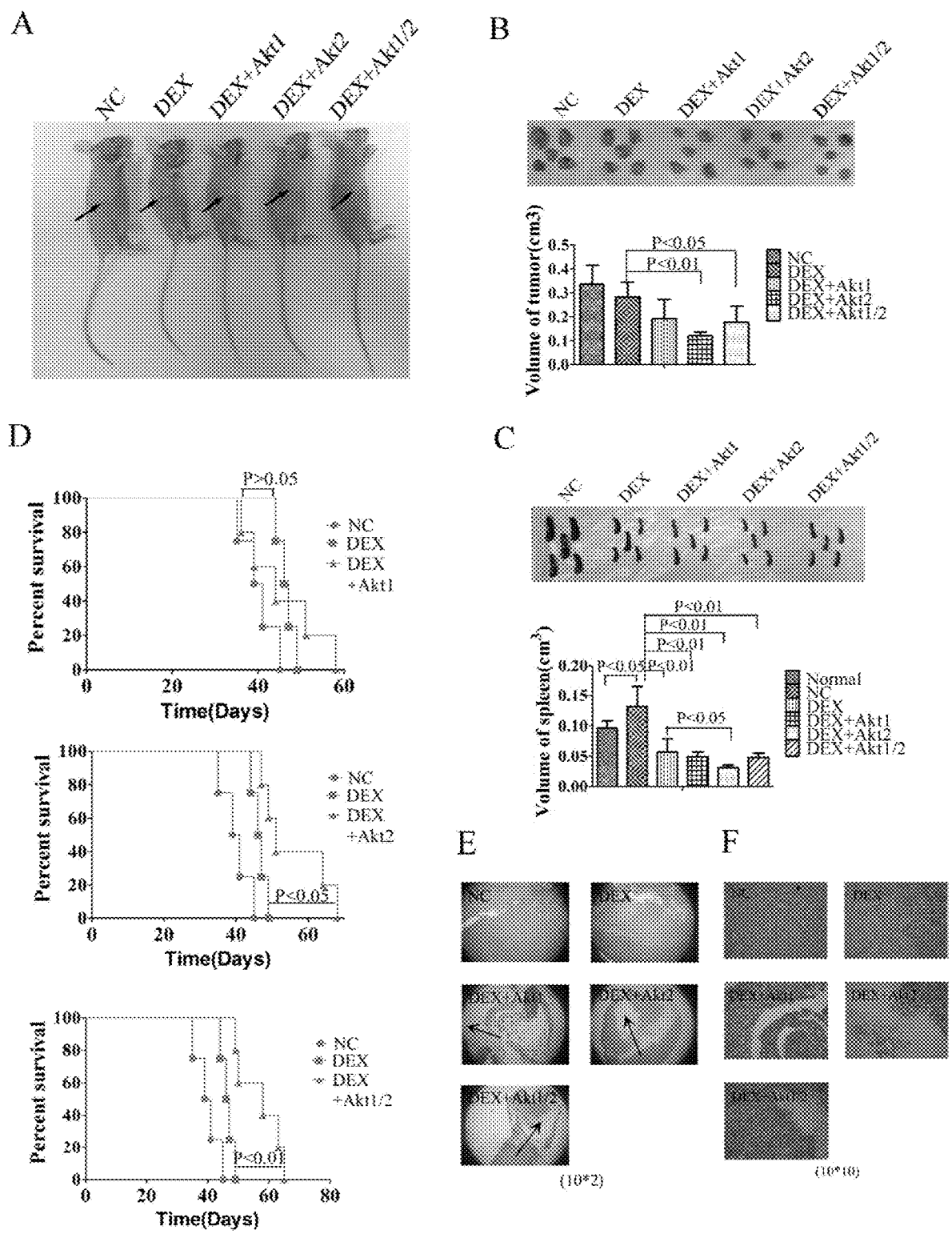
FIG. 7: the effect of an Akt inhibitor in combination with dexamethasone in nude mice.
Figure 7:
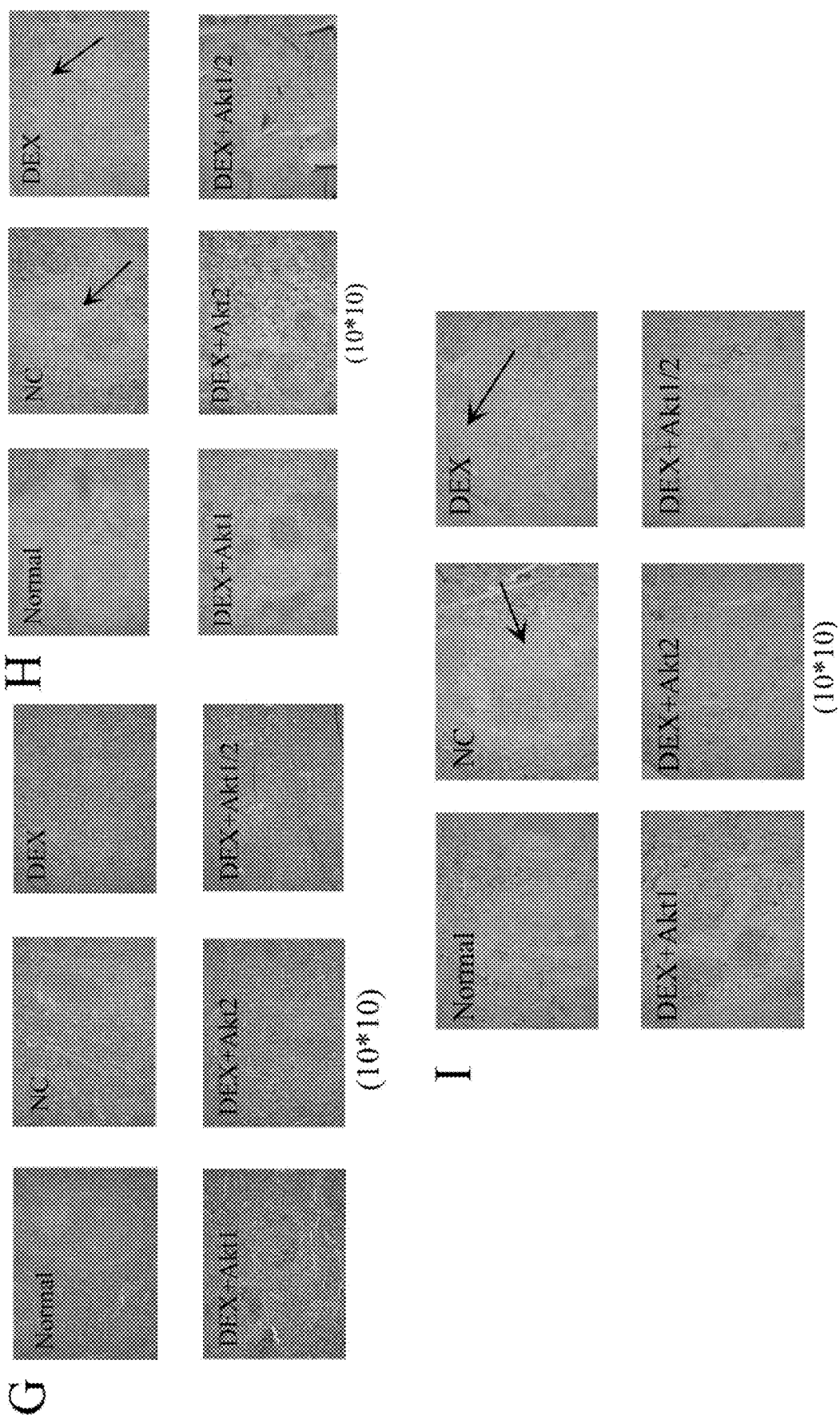

Results: as shown in FIGS. 7A and 7B, as compared to the NC group (injected with normal saline), the tumor sizes of the DEX+Akt1, DEX+Akt2 and DEX+Akt1/2 groups were significantly reduced ($p<0.01$, 0.01, 0.01); as compared to the DEX group, the tumor sizes of the DEX+Akt2 and DEX+Akt1/2 groups were significantly reduced ($p<0.01$, 0.05), and the tumor size of the DEX+Akt1 group was not significantly reduced ($p>0.05$).

As shown in FIG. 7C, as compared to the NC group, the spleen sizes of the DEX, DEX+Akt1, DEX+Akt2 and DEX+Akt1/2 groups were significantly reduced ($p<0.01$, 0.01, 0.01, 0.01); as compared to the DEX group, the spleen size of the DEX+Akt2 group was significantly reduced ($p<0.05$), and the spleen sizes of the DEX+Akt1 and DEX+Akt1/2 groups were not significantly reduced ($p>0.05$, 0.05).

As shown in FIG. 7D, the overall survival of tumor-bearing mice in the DEX+Akt2 and DEX+Akt1/2 groups was longer than that in the DEX group ($p<0.05$, 0.01).

Accordingly, the Akt subtype inhibitors could synergize with glucocorticoids in vivo to effectively promote the apoptosis of lymphocytes, the effect of Akt subtype inhibitors on glucocorticoid sensitization was significant, and amongst the Akt2 and Akt1/2 inhibitors exhibited a better sensitization effect than the Akt1 inhibitor.

CONCLUSIONS

1. As compared to the sensitive cell lines, the expression of intracellular Akt2 was significantly increased in the glucocorticoid-resistant tumor lymphocyte lines. The difference in expression of Akt2 in lymphocytes may affect and reflect the degree of sensitivity to glucocorticoids to a certain extent, the overexpression of Akt2 protein in the cells may be an important mechanism of producing glucocorticoid resistance in lymphocytes, and Akt2 may be used as a more accurate treatment target of reversing glucocorticoid resistance in lymphoma. Akt2 may also be used as an indicative for diagnosing whether lymphocytes are glucocorticoid resistant or not.

2. In the T-lymphoid tumor cells, the Akt2 subtype inhibitors significantly increased the sensitivity of glucocorticoid-induced lymphocyte apoptosis. In the drug-resistant cell lines, the combination of the Akt2 subtype inhibitor and glucocorticoid exhibited a good synergistic effect and were capable of reversing glucocorticoid resistance.

3. The Akt2 subtype inhibitor could significantly down-regulate the intracellular p-FoxO3a/total FoxO3a ratio, up-regulate the expression of pro-apoptosis protein Bim, and improve glucocorticoid-induced lymphocyte apoptosis by enhancing the intracellular FoxO3a/Bim signaling pathway, thererby increasing the sensitivity of lymphocytes to glucocorticoids.

4. Both in vivo and in vitro tests confirmed that the Akt2 subtype inhibitor has the minimal toxicity and has no effect on the blood system, liver functions, renal functions and blood glucose level in mice.

5. The Akt2 subtype inhibitor could synergize with dexamethasone to effectively reduce the tumor size and spleen size in the tumor-bearing mice, cause liquefaction and necrosis of the tumor and increase the overall survival; and the Akt2 subtype inhibitor is an agent that exhibits the best sensitization to glucocorticoid and the minimal toxic side effects.

The invention claimed is:

1. A pharmaceutical composition or kit for treating a glucocorticoid resistant tumor characterized by elevated Akt2 expression, comprising a selective Akt2 inhibitor, which enhances the intracellular FoxO3a/Bim signaling pathway and a glucocorticoid and optionally a pharmaceutically acceptable carrier, excipient and/or diluent.

2. The pharmaceutical composition or kit of claim 1, wherein the selective Akt2 inhibitor is selected from the group consisting of a small molecule compound, an antagonist of Akt2 protein, and a double-stranded RNA molecule that inhibits Akt2 mRNA, an antibody to Akt2 protein and an interference RNA molecule of Akt2 mRNA.

3. The pharmaceutical composition or kit of claim 1, wherein the glucocorticoid is selected from the group consisting of dexamethasone, betamethasone, triamcinolone, triamcinolone acetonide, beclomethasone, prednisolone, prednisone, methylprednisolone, hydrocortisone, cortisone acetate, budesonide, beclomethasone dipropionate, ciclesonide, cortisone, methylprednisolone, clobetasol butyrate, fluocinonide, beclomethasone dipropionate, mometasone furoate, halcinonide, clobetasol propionate, halcinonide, halometasone, diflorasone diacetate and derivatives thereof.

4. The pharmaceutical composition or kit of claim 1, wherein the tumor is a lymphocyte-derived tumor.

5. The pharmaceutical composition or kit of claim 1, wherein the selective Akt2 inhibitor is selected from the group consisting of the compound CCT128930 of the formula (II) and the nucleotide molecules set forth in SEQ ID NOs: 7 and 8

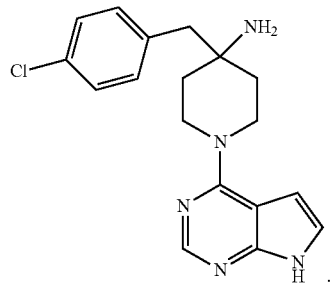

(II)

6. The pharmaceutical composition or kit of claim 1, wherein the tumor is acute lymphocytic leukemia, chronic lymphocytic leukemia, lymphoma or myeloma.

7. The pharmaceutical composition or kit of claim 1, wherein the tumor is B-cell lymphoma or T-cell lymphoma.

8. The pharmaceutical composition or kit of claim 1, wherein the tumor is a T-cell-derived tumor.

9. The pharmaceutical composition or kit of claim 1, wherein the tumor is Burkitt's lymphoma, T-lymphocytic leukemia, T-cell lymphoma or myeloma.

10. The pharmaceutical composition or kit of claim 9, wherein the tumor is acute T-lymphocytic leukemia.

11. A method for treating a glucocorticoid resistant tumor characterized by elevated Akt2 expression in a subject, comprising administrating a therapeutically effective amount of a selective Akt2 inhibitor, which enhances the intracellular FoxO3a/Bim signaling pathway and a glucocorticoid to the subject.

12. The method of claim 11, wherein the selective Akt2 inhibitor is selected from the group consisting of a small molecule compound, an antagonist of Akt2 protein, and a double-stranded RNA molecule that inhibits Akt2 mRNA, an antibody to Akt2 protein and an interference RNA molecule of Akt2 mRNA.

13. The method of claim 11, wherein the glucocorticoid is selected from the group consisting of dexamethasone, betamethasone, triamcinolone, triamcinolone acetonide, beclomethasone, prednisolone, prednisone, methylprednisolone, hydrocortisone, cortisone acetate, budesonide, beclomethasone dipropionate, ciclesonide, cortisone, methylprednisolone, clobetasol butyrate, fluocinonide, beclomethasone dipropionate, mometasone furoate, halcinonide, clobetasol propionate, halcinonide, halometasone, diflorasone diacetate and derivatives thereof.

14. The method of claim 11, wherein the tumor is a lymphocyte-derived tumor.

15. The method of claim 11, wherein the selective Akt2 inhibitor is selected from the group consisting of the compound CCT128930 of the formula (II) and the nucleotide molecules set forth in SEQ ID NOs: 7 and 8

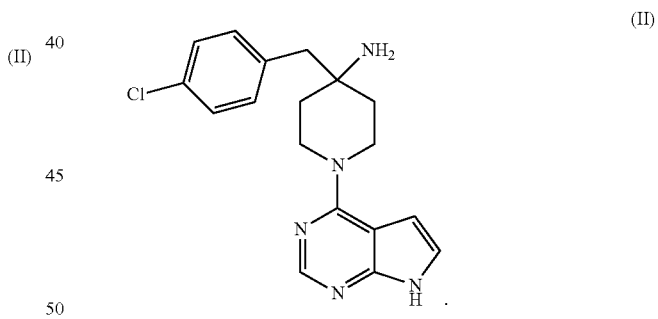

16. The method of claim 11, wherein the tumor is acute lymphocytic leukemia, chronic lymphocytic leukemia, lymphoma or myeloma.

17. The method of claim 11, wherein the tumor is B-cell lymphoma or T-cell lymphoma.

18. The method of claim 11, wherein the tumor is a T-cell-derived tumor.

19. The method of claim 11, wherein the tumor is Burkitt's lymphoma, T-lymphocytic leukemia, T-cell lymphoma or myeloma.

20. The method of claim 11, wherein the tumor is acute T-lymphocytic leukemia.

* * * * *